United States Patent
Handa et al.

(10) Patent No.: US 9,566,372 B2
(45) Date of Patent: Feb. 14, 2017

(54) SUSTAINED NITRIC OXIDE RELEASE COATING USING DIAZENIUMDIOLATE-DOPED POLYMER MATRIX WITH ESTER CAPPED POLY(LACTIC-CO-GLYCOLIC ACID) ADDITIVE

(71) Applicant: The Regents of the University of Michigan, Ann Arbor, MI (US)

(72) Inventors: Hitesh Handa, Ann Arbor, MI (US); Mark E. Meyerhoff, Ann Arbor, MI (US); Robert H. Bartlett, Ann Arbor, MI (US); Elizabeth J. Brisbois, Ann Arbor, MI (US); Lahdan Refahiyat, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 14/430,545

(22) PCT Filed: Sep. 25, 2013

(86) PCT No.: PCT/US2013/061665
§ 371 (c)(1),
(2) Date: Mar. 23, 2015

(87) PCT Pub. No.: WO2014/052443
PCT Pub. Date: Apr. 3, 2014

(65) Prior Publication Data
US 2015/0238662 A1 Aug. 27, 2015

Related U.S. Application Data

(60) Provisional application No. 61/707,192, filed on Sep. 28, 2012.

(51) Int. Cl.
| | | |
|---|---|---|
| *A61L 31/16* | (2006.01) | |
| *C08L 27/06* | (2006.01) | |
| *C08G 18/61* | (2006.01) | |
| *A61L 29/04* | (2006.01) | |
| *A61L 29/14* | (2006.01) | |
| *A61L 29/16* | (2006.01) | |
| *A61L 31/04* | (2006.01) | |
| *A61L 31/14* | (2006.01) | |

(52) U.S. Cl.
CPC .............. *A61L 31/16* (2013.01); *A61L 29/049* (2013.01); *A61L 29/141* (2013.01); *A61L 29/16* (2013.01); *A61L 31/041* (2013.01); *A61L 31/141* (2013.01); *C08G 18/61* (2013.01); *C08L 27/06* (2013.01); *A61L 2300/114* (2013.01); *A61L 2300/802* (2013.01)

(58) Field of Classification Search
CPC ...... A61L 29/16; A61L 29/141; A61L 29/049; A61L 31/16; A61L 31/141; A61L 31/041; A61L 2300/114; A61L 2300/802; C08G 18/61; C08L 27/06
See application file for complete search history.

(56) References Cited

U.S. PATENT DOCUMENTS

| | | | |
|---|---|---|---|
| 2006/0008529 A1* | 1/2006 | Meyerhoff | A61L 33/06 424/486 |
| 2011/0117164 A1 | 5/2011 | Meyerhoff et al. | |
| 2012/0070483 A1 | 3/2012 | Zhou et al. | |

OTHER PUBLICATIONS

Tracy, M.A., et al.; Biomaterials, 1999, p. 1057-1062.*
Martin, D.J., et al; Biomaterials, 2000, p. 1021-1029.*
Cai, W. et al., "Diazeniumdiolate-doped poly(lactic-co-glycolic acid)-based nitric oxide releasing films as antibiofilm coating", Biomaterials, 2012, vol. 33, Issue 32, pp. 7933-7944.
Yan, Q., et al., "Intravascular glucose/lactate sensors, prepared with nitric oxide releasing poly(lactide-co-glycolide)-based coatings for enhanced biocompatibility", Biosensors and Bioelectronics, 2011, vol. 26, Issue 111, pp. 4276-4282.

* cited by examiner

*Primary Examiner* — Robert Jones, Jr.
(74) *Attorney, Agent, or Firm* — Dierker & Kavanaugh, P.C.

(57) ABSTRACT

A polymeric composition includes a polymer matrix having a lipophilic discrete nitric oxide adduct and/or a polymeric nitric oxide adduct associated therewith, by covalent attachment to the polymer matrix and/or by dispersion within the polymer matrix, with the discrete nitric oxide adduct and/or the polymeric nitric oxide adduct being capable of releasing nitric oxide (NO). The polymeric composition further includes an ester capped poly(lactide-co-glycolide) (PLGA) additive to at least one of increase, prolong, and control NO release rates from the lipophilic discrete nitric oxide adduct and/or the polymeric nitric oxide adduct.

15 Claims, 12 Drawing Sheets

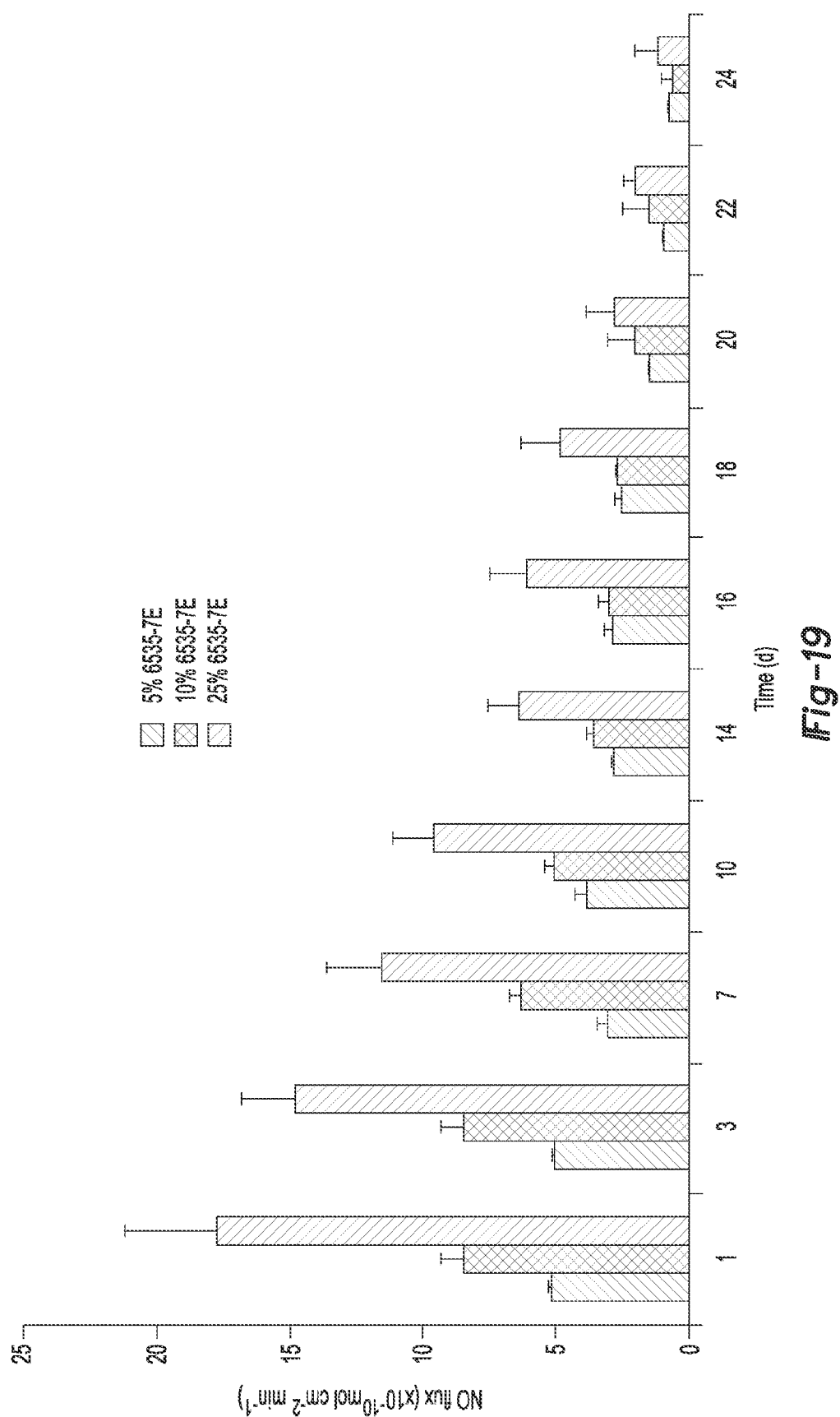

SUSTAINED NITRIC OXIDE RELEASE COATING USING DIAZENIUMDIOLATE-DOPED POLYMER MATRIX WITH ESTER CAPPED POLY(LACTIC-CO-GLYCOLIC ACID) ADDITIVE

CROSS-REFERENCE TO RELATED APPLICATION

This application claims the benefit of U.S. Provisional Application Ser. No. 61/707,192, filed Sep. 28, 2012, which is incorporated by reference herein.

STATEMENT REGARDING FEDERALLY SPONSORED RESEARCH OR DEVELOPMENT

This invention was made with government support under HL015434, EB000783 and K25HL111213 awarded by the National Institutes of Health. The government has certain rights in the invention.

BACKGROUND

Nitric oxide (NO) has been shown to have several important physiological functions, including its unique vasodilating properties, cancer-fighting potency, anti-platelet activity and antimicrobial/antiviral effects. Although NO is a stable radical, it may be highly reactive with hemoglobin and oxygen, thus making delivery of NO to the target site challenging. Stable hydrophilic, as well as hydrophobic NO donors may be best to take advantage of the potency of NO for a wide range of biomedical applications. These include NO-releasing pharmaceuticals and the preparation of thromboresistive hydrophobic polymeric coatings for medical devices such as intravascular catheters and extracorporeal circuits (based on NO's antiplatelet activity). However, despite the benefits of NO, the use of NO donors in polymeric systems has been relatively limited for various reasons.

BRIEF DESCRIPTION OF THE DRAWINGS

Features and advantages of examples of the present disclosure will become apparent by reference to the following detailed description and drawings, in which:

(FIG. 7A) is an image of thrombus area in 3/8 inch I.D. tubing in the control ECC; (FIG. 7B) is an image of thrombus area in 3/8 inch I.D. NOrel polymer ECC; and (FIG. 7C) shows quantification of thrombus area as calculated with NIH Image J software using a 2D representation of thrombus (the data are means±SEM, *=p<0.05, control ECC vs. NOrel ECC after 4 hours ECC flow);

FIG. 19 shows NO release profiles of SP-60D-20 polymer films doped with 25 wt % DBHD/N$_2$O$_2$ and 5, 10, or 25 wt % 6535DLG7E (the data are means±SEM).

DETAILED DESCRIPTION

Figure 1:
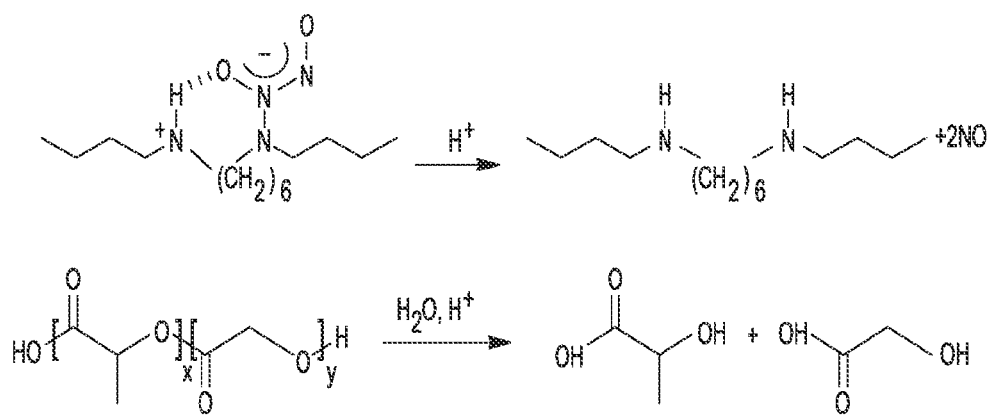
FIG. 1 is a reaction mechanism of diazeniumdiolated dibutylhexanediamine (DBHD/$N_2O_2$) (top) and poly(lactic-co-glycolic acid) (PLGA) (bottom; x=lactic acid units and y=glycolic acid units)

Nitric oxide (NO) is an endogenous vasodilator that exhibits potent antimicrobial/antiviral activities, and further serves as a natural inhibitor of platelet adhesion and activation. Nitric oxide can be released from an NO donor species (e.g., diazeniumdiolated dibutylhexanediamine, other lipophilic diazeniumdiolate structures, diazeniumdiolate appended to polymers (e.g., polymethacrylate polymers with pendant diazeniumdiolates), diazeniumdiolated N-(6-aminohexyl)-3-aminopropyl-trimethoxysilane, etc.) within a polymer coating. Examples of the present disclosure use an FDA approved and non-toxic additive, poly(lactic-co-glycolic acid) (PLGA), for its ability to help sustain NO release by maintaining a lower pH inside the base polymer material (an example of which is poly(vinyl chloride) (PVC)).

Various hydrophobic polymer materials may be employed in the material, method, and device as disclosed herein. These include, but are not limited to materials such as poly(vinyl chloride) (PVC), silicone rubbers (SR), polyurethanes (PU), polymethacrylates, polyacrylates, polycaprolactones, and/or mixtures thereof. In addition, polymers that have both hydrophobic and hydrophilic segments, such as polyurethanes that possess greater water uptake because of increased soft to hard segment ratios (e.g., Tecophillic SP-60D-60 polyurethane and SP-60D-20 polyurethane commercially available from The Lubrizol Corporation, Wickliffe, Ohio) can also be used. The polymer of choice will be one capable of releasing NO from, for example, covalently attached and/or dispersed diazeniumdiolate type NO-adducts/donors within the polymer.

"Nitric oxide adducts" (NO adducts) and "NO-donors" refer to compounds and functional groups which, under physiological conditions, can donate and/or release NO such that biological activity of the NO is expressed at the intended site of action/target site.

Examples according to the present disclosure include an NO donor/adduct within a polymer coating. The NO donor/adduct may be integrated into the polymer coating in any suitable manner, an example of which is doping. Suitable NO adducts (examples of which include lipophilic adducts) are generally those exhibiting capability of embedding (either by covalent attachment and/or dispersion) into the polymer matrix and exhibiting process preparation stability.

"Lipophilic NO adducts" as referred to herein are those NO adducts (examples of which are diazeniumdiolates) which, when placed into a polymer matrix, release therapeutically relevant fluxes of NO, in the range of about 0.2-20×10$^{-10}$ mol/cm$^2$-min of NO from the polymer phase. Those compounds that have their NO-releasing moiety covalently attached to a polymer backbone are generally referred to as "polymeric NO adducts." Examples of suitable polymeric NO adducts include, but are not limited to, diazeniumdiolated silicone rubbers (DACA/N$_2$O$_2$), diazeniumdiolated polymethacrylates, diazeniumdiolated polyurethanes, diazeniumdiolated poly(vinyl chloride), and/or mixtures thereof.

Further, a system is contemplated as being within the purview of the present disclosure that includes discrete lipophilic diazeniumdiolate doped into a polymer, with the polymer also having diazeniumdiolate appended thereto (e.g., by covalent attachment). For example, previously prepared polymethacrylate polymers with appended diazeniumdiolate functional groups can be mixed with discrete, lipophilic DBHD/N$_2$O$_2$ (diazeniumdiolated dibutylhexane diamine) or similar diazeniumdiolated species to create the long-term NO release polymers enabled by the present disclosure.

It is to be understood that generally the polymeric NO adducts do not have a protecting group(s) attached thereto. However, in an example in which the polymeric NO adducts have a benign protecting group, it is to be understood that when the protecting group is released, a benign species is yielded. Still further, the benign protecting group of an NO polymeric adduct may be removed prior to and/or during NO release. Furthermore, if a protecting group is utilized that is non-benign, it is to be understood that the protecting group is removed prior to application of the device (e.g., prior to NO release).

Examples of suitable benign protecting groups include, but are not limited to sugar or sacharride protecting groups (e.g., glycosylated protecting groups that contain glucose, galactose, or mannose), glycosylated protecting groups that are derivatized sugar protecting groups (e.g., acetylated glucose, galactose, or mannose), and/or mixtures thereof. Specific examples of the sugar protecting groups include O$_2$-B-galactosepyranosyl and O$_2$-a-D-mannopyranosyl.

Examples of suitable non-benign protecting groups include, but are not limited to O$_2$-vinyl groups, O$_2$-acetoxymethyl groups, and/or mixtures thereof. Specific examples of non-benign protecting groups include O$_2$-aryl derivatives such as O$_2$-[2,4-dinitrophenyl], O$_2$-[2-Nitro-4 (trifluoromethyl)phenyl], O$_2$-[3-nitropyrid-2yl], 1-(2-Bromoethoxy), and/or mixtures thereof.

The NO adduct of choice is one capable of spontaneous release of NO when the polymer is exposed to solutions and/or blood under physiological conditions. Some examples of NO adducts include protected and discrete N-diazeniumdiolates, C-based diazeniumdiolates, and/or mixtures thereof. An example of a suitable NO adduct is diazeniumdiolated dibutylhexanediamine (DBHD/N$_2$O$_2$).

It is further believed that examples of the present disclosure including ester capped PLGA may help stabilize (e.g., due to the acid environment) a different class of NO adduct species, S-nitrosothiols (RSNO), thus advantageously allowing longer NO release from the RSNO species.

Spontaneous release of NO from the polymer may be governed by at least one process occurring between the NO adduct and the aqueous environment. These include, but are not limited to at least one of diffusion and ionization of water into/within the organic polymer; ion-exchange between the buffer ions in surrounding aqueous/blood phase and ions within the polymer; protonation of amine-nitrogen-bearing compounds to yield NO; and deprotonation of water by secondary amine sites to yield organic ammonium hydroxides. Suitable nitrogen-bearing compounds include, but are not limited to, various diazeniumdiolates.

It is to be understood that discrete nitric oxide adducts may be either covalently attached to the polymer matrix or may be dispersed therein, or both. Some examples of discrete diazeniumdiolates include, but are not limited to anionic diazeniumdiolates stabilized with metal cations, zwitterionic diazeniumdiolates, and protected discrete diazeniumdiolates (e.g., $O^2$ protected discrete diazeniumdiolates). In an example incorporating protected nitric oxide adducts (such as protected N-diazeniumdiolates), it is to be understood that the protected nitric oxide adducts may be dispersed substantially throughout the polymer matrix.

Examples of parent structures used to form diazeniumdiolates may be any primary or secondary amine containing compounds, including, but not limited to:

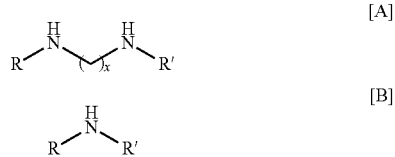

where R and R' may be hydrogen; n-alkyls; branched alkyls; aliphatics; cyclic and/or aromatic amine side-chains; ketones; aldehydes; amides; ether; esters; alkenes; alkynes; and/or mixtures thereof; and/or the like.

Examples of the diazeniumdiolates that may be formed from parent structure A include the following:

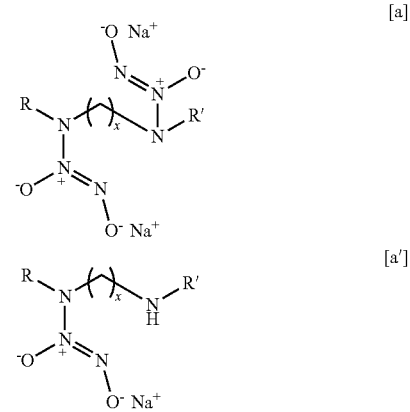

Examples of the diazeniumdiolates that may be formed from parent structure B include the following:

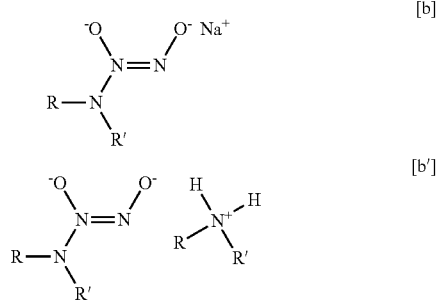

As an example, a sodium ion is depicted in structures a, a', b, and b' as a counter ion in order to stabilize the respective diazeniumdiolates. It is to be understood that other metal ions such as ions of lithium, potassium, copper, and/or the like, and/or mixtures thereof, may be valid metal cations to stabilize the species.

As depicted, anionic diazeniumdiolates with a diamine backbone or compounds containing one amine site or those containing three or more amine sites may be used in examples of the present disclosure.

The diazeniumdiolate and PLGA-doped NO release (NOrel) PVC coating according to examples of the present disclosure was evaluated in vitro and within a short-term (4 hours ECC) and long-term (9 day catheters) in vivo rabbit model of thrombogenicity. The pH change with the coating was visualized by incorporating pH sensitive probes into the films. The observed pH changes of the films are correlated with the observed NO release profile. The NOrel coatings continuously released $7\text{-}18\times10^{-10}$ mol cm$^{-2}$ min$^{-1}$ NO for 14 days at 37° C. in phosphate-buffered saline (PBS). The new NOrel materials were employed as inner wall coatings of extracorporeal circuits used for 4 hours of extracorporeal circulation (ECC) in a rabbit model of thrombogenicity to examine the effect of the coatings on platelet function, clotting and fibrinogen adsorption. Four out of 7 control circuits clotted within 3 hours, whereas all the NOrel coated circuits were patent after 4 hours. Platelet count after 4 hours on the NOrel ECC were preserved (79±11% as compared to 54±6% on control circuits). After 9 days of catheter implantation, NOrel catheters were found to have significantly reduced thrombus area (about 7 times smaller) and a 1.3 log reduction in bacterial adhesion (a 94% reduction as compared to catheters without an example of the NOrel coating of the present disclosure). The NOrel coatings according to examples of the present disclosure showed a significant decrease in the thrombus area as compared to the controls (1.5 pixels/cm$^2$ vs. 6.5 pixels/cm$^2$). Results suggest that by using PLGA as an additive to a PVC material containing a lipophilic diazeniumdiolate, the NO release can be prolonged for up to 2 weeks by controlling the pH within the polymeric coating.

Blood/material interaction is important to the success of implantable medical devices, ranging from simple catheters, stents and grafts, to complex extracorporeal artificial organs that are used in thousands of patients every day. Thrombosis is one of the primary problems associated with clinical application of blood contacting materials. Despite a thorough understanding of the mechanisms of blood-surface interactions and decades of bioengineering research effort, the ideal non-thrombogenic prosthetic surface remains an unsolved problem. Over the last 50 years, much has been learned about surface-induced thrombosis and attempts to prevent it with systemic anticoagulation and surface modifications. Surface modifications have included using pure, very smooth silicone rubber or polyurethane, pre-exposure of the surfaces to albumin and other coating proteins, and surface binding of heparin in an ionic as well as a covalent fashion. Despite extensive research to develop a non-thrombogenic surface that mimics the endothelium, none of these modifications have been successful.

Nitric oxide (NO) has been found to be one of two potent vasodilators secreted by normal endothelium that has the ability to inhibit platelet adhesion and aggregation to the blood vessel wall. It is also produced by cells within the sinus cavities as well as by macrophages and neutrophils to kill foreign bacteria and viruses. The NO-flux from a normal and stimulated endothelium has been estimated to be in the range of $0.5\times10^{-10}$ mol cm$^{-2}$ min$^{-1}$ to $4\times10^{-10}$ mol cm$^{-2}$ min$^{-1}$. Nitric oxide has been extensively studied for its inhibitory effects on circulating platelet and monocyte activation that leads to aggregation and ultimately initiation of thrombosis. A wide range of NO donors such as S-nitrosothiols, N-hydroxy-N-nitrosoamines, N-diazeniumdiolates and nitrosyl metal complexes have been studied over the past decade.

Diazeniumdiolates are one of the most widely studied NO donors. NO can be released from an NO donor compound, diazeniumdiolated dibutylhexanediamine (DBHD/$N_2O_2$) (see FIG. 1, top). While DBHD/$N_2O_2$ is an excellent donor for incorporation into hydrophobic polymers to create NO release coatings, the loss of NO from this molecule creates free lipophilic amine species within the polymer that react with water, thereby increasing the pH within the organic polymer phase. This pH increase effectively turns off the NO production before a significant fraction of the total NO payload has been released. To overcome this complication, tetrakis-(p-chlorophenyl)-borate has been used as an additive to maintain a low enough pH within the organic polymer phase and to maintain a sustained NO flux. However, tetrakis-(p-chlorophenyl)-borate may be cytotoxic towards endothelial and smooth muscle cells.

Examples of the present disclosure focus on a completely different approach to address this pH control problem. Examples of the present method use ester capped poly(lactic-co-glycolic acid) (PLGA) species as additives to help stabilize the pH within the organic phase polymeric coatings. The addition of PLGA can be used to control the flux of NO emitted from polymers containing diazeniumdiolate species by helping to control the pH within the polymer phase. Ester capped PLGA is not only non-toxic but can also sustain the NO flux for a prolonged period (a major requirement of long-term applications) by the slow formation of lactic acid and glycolic acid within the base polymer layer of the coating (see FIGS. 1 (bottom) and 1A).

Figure 1A:
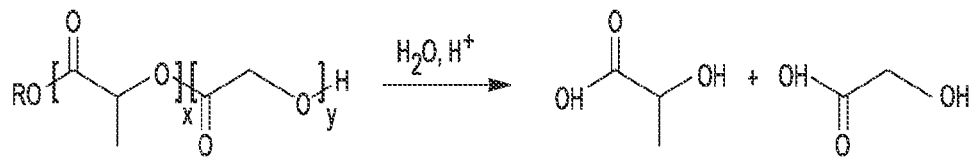
FIG. 1A is a reaction mechanism of an example of ester capped poly(lactic-co-glycolic acid) (PLGA) (x=lactic acid units and y=glycolic acid units)

Hydrolysis of a general example of an ester capped PLGA is shown in FIG. 1A. It is to be understood that the R in the ester group may be any suitable group, including, for example, ethyl, propyl, and butyl groups; lauryl groups or any other long change fatty acid group; sulfonic acid groups; phosphoric acid groups; or combinations thereof. The 5050DLG7E (1-2 month) and 6535DLG7E (3-4 month) PLGA additive tested in the Examples herein had a lauryl ester end group. However, it is to be understood that the examples of the present disclosure are not intended to be limited to PLGA additives having lauryl ester end groups.

Ester linkages of the PLGA are hydrolyzed as small amounts of water penetrate the polymer from the surrounding aqueous environment to generate lactic acid and glycolic acid within the polymer matrix. The presence of this continuous acid production reaction compensates for the increase in pH from generation of organo-ammonium hydroxide (reaction of liberated free amines from DBHD with water in the polymer film) from the NO release reaction, thereby maintaining a greater rate of NO release for longer periods of time.

In prior methods, there were two main strategies utilizing PLGA to deliver NO from diazeniumdiolate species. The first strategy is using PLGA microparticles (acid form) to locally deliver the NO donor compound. An example of this first strategy employed PLGA microparticles having an NO donor (diethylenetriamine (DETA) NONOate) to deliver NO for a very short (e.g., 6 hours) period. In another example of the first strategy, stents were loaded with N-ethyl-2-(1-ethyl-2-hydroxy-2-nitrosohydrazino) ethanamine (NOC-12) as an NO donor inside PLGA-PEG microspheres to deliver the NO donor compound. An important requirement of this first strategy is that the NO donor compound be biocompatible. In the second strategy, it was shown that PLGA (acid form) has the potential to act as a proton donor to enhance the release of NO from a polymer material that had covalently linked diazeniumdiolate groups; however, this was for a short (e.g., 20 hours) period.

In contrast, examples of the present disclosure use ester capped PLGA as an additive in a polymer matrix (e.g., a PVC/DOS (dioctyl sebacate) matrix) to control NO release from a lipophilic diazeniumdiolate (e.g., DBHD/$N_2O_2$) species added to the organic film. The present inventors have shown herein that the hydrolysis rate and acid content of the given PLGA species used greatly influences the NO release profile. Examples of film compositions according to the present disclosure can advantageously and unexpectedly sustain high fluxes of NO for up to 14 days by using PLGAs with little or no free acid sites (ester capped) and low monomer acid levels, so as not to cause a large initial burst of NO (lower pH in polymer film initially). Further, incorporation of pH indicators in the coatings provides a means to correlate the NO release with the pH change within the PVC matrix. The newly formulated PLGA/diaziumdiolate doped PVC coatings according to examples of the present disclosure are tested in an in vivo rabbit ECC model to assess platelet count and function preservation, in addition to reduction in the thrombus coverage area. Use of ester capped PLGAs with slower hydrolysis times in coatings according to examples of the present disclosure are shown to be an effective additive to control the pH and sustain NO release from the coatings.

To further illustrate the present disclosure, various examples are given herein. It is to be understood that these examples are provided for illustrative purposes and are not to be construed as limiting the scope of the present disclosure.

EXAMPLES

Materials

Tygon® poly(vinyl chloride) (PVC) tubing was purchased from Fisher Healthcare (Houston, Tex.). High molecular weight poly(vinyl chloride) (PVC), dioctyl sebacate (DOS), anhydrous tetrahydrofuran (THF), anhydrous acetonitrile, bromothymol blue, bromocresol green, sodium chloride, potassium chloride, sodium phosphate dibasic, and potassium phosphate monobasic were purchased from Sigma-Aldrich Chemical Company (St. Louis, Mo.). Various poly(D,L-lactide-co-glycolide) materials, including 5050DLG1A (acid form; 50:50 ratio of lactic acid monomer to glycolic acid monomer), 5050DLG7E (ester capped; 50:50 ratio of lactic acid monomer to glycolic acid monomer), and 6535DLG7E (ester capped; 65:35 ratio of lactic acid monomer to glycolic acid monomer) were obtained from SurModics Pharmaceuticals Inc. (Birmingham, Ala.). N,N'-Dibutyl-1,6-hexanediamine (DBHD) was purchased from Alfa Aesar (Ward Hill, Mass.). Tecophilic SP-60D-60, Tecophilic SP-60D-20, and Tecoflex SG-80A were purchased from Lubrizol Advanced Materials Inc. (Cleveland, Ohio). Elast-eon™ E2As was obtained from AorTech International, plc (Scoresby, Victoria, Australia). The mouse antibodies for human CD61 (GPIIIa) FITC and human P-selectin glycoprotein (CD62P) PE were obtained from AbD Serotec (Raleigh, N.C.). AbD Serotec was also the source for mouse isotype controls for $IgG_1$ FITC and $IgG_1$ PE. Human plasma fibrinogen containing ≥90% clottable proteins was obtained from Calbiochem (La Jolla, Calif.) and fluorescein-labeled goat IgG (polyclonal) against denatured human fibrinogen was purchased from MP Biomedicals, LLC (Solon, Ohio). The 96-well microtiter plates (black, polypropylene) used for fluorescence measurements were obtained from Nalge Nunc International (Rochester, N.Y.). DBHD/$N_2O_2$ was synthesized by treating DBHD with 80 psi NO gas purchased from Cryogenic Gases (Detroit, Mich.) at room temperature for 48 hours.

Preparation of NOrel Films for NO Release and pH Studies

Active layer film formulations consisting of 10 wt % PLGA (5050DLG1A, 5050DLG7E, or 6535DLG7E)+25 wt % DBHD/$N_2O_2$ in 2:1 PVC/DOS were prepared with 80 mg PLGA, 200 mg DBHD/$N_2O_2$, 173 mg DOS and 347 mg PVC in 5 mL THF. The 10 wt % PLGA control film solution consisted of 80 mg PLGA, 240 mg DOS and 480 mg PVC in 5 mL THF. The 25 wt % DBHD/$N_2O_2$ only film consisted of 200 mg DBHD/$N_2O_2$, 200 mg DOS, and 400 mg PVC in 5 mL THF. The active layer solutions were cast in Teflon rings (diameter=2.5 cm) and cured for 2 days under ambient conditions. Disks (diameter=0.9 cm) were cut from the active layer film and dip coated 8 times with the top coating solution (375 mg DOS, 750 mg PVC in 15 mL THF). Top coated films were dried under ambient conditions for 1 day. The final films had an active layer thickness of about 600 μm and topcoat thickness of about 200 μm.

For the pH studies, the films were prepared as described above with the exception of adding given pH indicators to the active layer solution. The pH indicators, bromocresol green or bromothymol blue, were present in the active layer casting solution at 0.025 wt %. Photos of the pH films were taken each day to monitor the change in pH as indicated by the color of the incorporated pH indicators.

Acid Content of PLGA

The acid number, which is a measure of the initial acid content of the PLGA and is directly related to the free carboxylic acid functionalities, was determined by the following titration method. Approximately 50 mg of PLGA was dissolved in 10 mL of a 1:1 mixture of acetone and THF. This solution was immediately titrated with 0.01 N KOH in methanol to a stable pink endpoint. Phenolphthalein in methanol (0.1 wt %) was used as the indicator for the titration. Titrations were performed in triplicate.

Preparation of NOrel Coated ECC Loops

A plasticized PVC coating containing 25 wt % DBHD/$N_2O_2$, an NO donor, was prepared using the following method. Triple layers of polymeric coatings that included a base layer, active layer and top layer were individually coated onto the inner surface of the Tygon® tubing that formed the ECC. The base layer was prepared by dissolving 600 mg PVC in 10 mL THF (Solution A). The active layer containing the NO donor was prepared by dissolving 770 mg PVC, 385 mg DOS and 180 mg PLGA in 10 mL THF. Four hundred and fifty milligrams DBHD/$N_2O_2$ was then dispersed within the polymer cocktail by sonication for 30 minutes to obtain a slightly cloudy dispersion of the diazeniumdiolate in the solution (Solution B). The top coat solution was prepared using 181 mg PVC, 362 mg DOS plasticizer and 10 mL THF (Solution C).

The ECC configuration used in this study (with rabbits) consisted of 16-gauge and 14-gauge IV polyurethane angiocatheters (Kendall Monoject, obtained from Tyco Healthcare Mansfield, Mass.), two 16 cm in length, ¼ inch inner diameter (ID) Tygon® tubing and an 8 cm length of ⅜ inch ID Tygon®, tubing which created a thrombogenicity chamber where thrombus could form more easily due to more turbulent blood flow. The ECC was pieced together, starting at the left carotid artery side, with the 16-gauge angiocatheter, one 15 cm length ¼ inch ID tubing, the 8 cm length thrombogenicity chamber, the second 15 cm length ¼ inch ID tubing, and finally the 14-gauge angiocatheter. The angiocatheters were interfaced with tubing using 2 Luer-lock PVC connectors. The ⅜ inch ID tubing and the ¼ inch tubing were welded together using THF.

The assembled ECC was coated first with a base coating of Solution A, followed by two coats of the active layer of Solution B and the top coat (Solution C). The circuitry was filled with each solution, which was then removed. Each coat was allowed to dry for at least 1 hour. The finished ECCs were allowed to cure under nitrogen for 20 minutes and then dried under vacuum for 2 days. The trilayer configuration had a total thickness of approximately 150 μm to 200 μm.

NO Release Measurements

Nitric oxide released from the films was measured using a Sievers chemiluminescence Nitric Oxide Analyzer (NOA), model 280 (Boulder, Colo.). A sample of the film was placed in 4 mL PBS buffer at 37° C. Nitric oxide liberated from the film was continuously swept from the headspace of the sample cell and purged from the buffer with a nitrogen sweep gas and bubbler into the chemiluminescence detection chamber. The flow rate was set to 200 mL/min with a chamber pressure of 5.4 Torr and an oxygen pressure of 6.0 psi. Films were incubated in 4 mL of PBS buffer at 37° C. for a 2 week period and tested for NO release at various time points. Buffer was replaced every day. In addition, a uniform segment of ECC loop was tested for 4 hours in vitro for NO release. After the surgery, a section of the ECC loop was tested for NO release post blood exposure.

In Vitro Fibrinogen Adsorption Assay

The in vitro fibrinogen adsorption immunofluorescence assay was performed in a 96-well format. The NOrel and control polymer solutions used to prepare the ECC circuits were also employed to coat microwells of the 96-well microtiter plates. In addition, similar polymer drying conditions were used for the ECC and 96-well preparations. Briefly, human fibrinogen was diluted to 3 mg/mL with Dulbecco's phosphate-buffered saline (dPBS) without $CaCl_2$ and $MgCl_2$ (Gibco Invitrogen, Grand Island, N.Y.), equivalent to the human plasma concentration, and then used for the adsorption experiments. One hundred μL of this solution were added to each well for 1.5 hours at 37° C., followed by eight washing steps using 100 μL of wash buffer for each wash, which consisted of a 10-fold dilution of the AbD Serotec Block ACE buffer (Raleigh, N.C.) containing 0.05% Tween 20 (Calbiochem La Jolla, Calif.). To block nonspecific antibody binding, wells were incubated with 100 μL of blocking buffer (4-fold dilution of Serotec Block ACE buffer) for 30 minutes at 37° C. After rinsing 3 times with wash buffer (100 μL per well) a background fluorescence measurement of the plates was performed at 485 nm (excitation) and 528 nm (emission) on a Synergy 2 fluorescence microplate reader (Biotek, Winooski, Vt.). To detect the adsorbed fibrinogen, goat antihuman fibrinogen antibody was diluted (1:10) in a 10-fold dilution of the Serotec Block ACE buffer, and 100 μL of this final solution was added to each well. The antibody was allowed to bind to the surface-adsorbed fibrinogen for 1.5 hours at 37° C. Human fibrinogen adsorption to non-coated polypropylene was used as an internal control to normalize the fluorescence signals within different plates. A standard curve for fibrinogen was obtained on each plate from 0 μg/mL to 3000 μg/mL. All measurements were conducted in triplicate.

Short-Term ECC Rabbit Thrombogenicity Model

The animal handling and surgical procedures were approved by the University Committee on the Use and Care of Animals (UCUCA), in accordance with university and federal regulations. A total of 12 Zealand white rabbits (Myrtle's Rabbitry, Thompson's Station, Tenn.) were used in this study. All rabbits (2.5-3.5 kg) were initially anesthetized with intramuscular injections of 5 mg/kg xylazine injectable (AnaSed®, Lloyd Laboratories Shenandoah, Iowa) and 30 mg/kg ketamine hydrochloride (Hospira, Inc., Lake Forest, Ill.). Maintenance anesthesia was administered via isoflurane gas inhalation at a rate of 1.5-3% via mechanical ventilation, which was done via a tracheotomy and using an A.D.S. 2000 Ventilator (Engler Engineering Corp., Hialeah, Fla.). Peek inspiratory pressure was set to 15 cm of $H_2O$, and the ventilator flow rate was set to 8 L/min. In order to aid in maintenance of blood pressure stability, IV fluids of Lactated Ringer's were given at a rate of 10 mL/kg/hour. For monitoring blood pressure and collecting blood samples, the rabbits' right carotid artery was cannulated using a 16-gauge IV angiocatheter (Jelco®, Johnson & Johnson, Cincinnati, Ohio). Blood pressure and derived heart rate were monitored with a Series 7000 Monitor (Marquette Electronics, Milwaukee, Wis.). Body temperature was monitored with a rectal probe and maintained at 37° C. using a water jacketed heating blanket.

Prior to placement of the arteriovenous (AV) custom-built extracorporeal circuit (ECC), the rabbit left carotid artery and right external jugular vein were isolated, and baseline hemodynamics as well as arterial blood pH, $pCO_2$, $pO_2$, total hemoglobin and methemoglobin were measured using an ABL 825 blood-gas analyzer and an OSM3 Hemoximeter (Radiometer Copenhagen, Copenhagen, DK). In addition, baseline blood samples were collected for platelet and total white blood cell (WBC) counts which were measured on a Coulter Counter Z1 (Coulter Electronics, Hialeah, Fla.). Plasma fibrinogen levels were determined using a Dade Behring BCS Coagulation Analyzer (Siemens, Deerfield, Ill.), activated clotting times (ACT) were monitored using a Hemochron Blood Coagulation System Model 801 (International Technidyne Corp., Edison, N.J.), platelet function was assessed using a Chrono-Log optical aggregometer model 490 (Havertown, Pa.).

After baseline blood measurements, the AV custom-built ECC was placed into position by cannulating the left carotid artery for ECC inflow and the right external jugular vein for ECC outflow. The flow through the ECC was initiated by unclamping the arterial and venous sides of ECC, and blood flow in circuit was monitored with an ultrasonic flow probe and flow meter (Transonic HT207, Ithaca, N.Y.). Animals were not systemically anticoagulated during the experiments.

After 4 hours on ECC, the circuits were clamped, removed from animal, rinsed with 60 mL of saline and drained. Any residual thrombus in the larger tubing of ECC (i.e., thrombogenicity chamber) was photographed, and the degree of thrombus image was quantitated using Image J imaging software from National Institutes of Health (Bethesda, Md.). Prior to euthanasia, all animals were given a dose of 400 U/kg sodium heparin to prevent necrotic thrombosis. The animals were euthanized using a dose of Fatal Plus (130 mg/kg sodium pentobarbital) (Vortech Pharmaceuticals, Dearborn, Mich.). All animals underwent gross necropsy after being euthanized, including examination of the lungs, heart, liver and spleen for any signs of thromboembolic events.

Blood Sampling

Rabbit whole blood samples were collected in non-anticoagulated 1 cc syringes for ACT, 3.2% sodium citrate vacutainers (Becton, Dickinson, Franklin Lakes, N.J.) in 3 cc volumes for cell counts, aggregometry, and 1 cc syringes containing 40 U/mL of sodium heparin (APP Pharmaceuticals, LLC, Schaumburg, Ill.) for blood-gas analysis. Following the initiation of ECC blood flow, blood samples were collected every hour for 4 hours for in vitro measurements. Samples were used within 2 hours of collection to avoid any activation of platelets, monocytes or plasma fibrinogen.

Platelet Aggregometry

Rabbit platelet aggregation was assayed based on the Born's turbidimetric method using a Chrono-Log optical aggregometer. Briefly, citrated blood (1:10 blood to ACD) was collected (6 mL), and platelet-rich plasma (PRP) was obtained by centrifugation at 110×g for 15 minutes. Platelet-poor plasma (PPP) was obtained by another centrifugation of the PRP-removed blood sample at 2730×g for 15 minutes and was used as the blank for aggregation. PRP was incubated for 10 minutes at 37° C. and then 40 µg/mL collagen (Chrono-PAR #385, Havertown, Pa.) was added. The percentage of aggregation was determined 3 minutes after the addition of collagen using Chrono-Log Aggrolink software.

Statistical Analysis

Data are expressed as mean±SEM (standard error of the mean). Comparison of ECC results between the various NOrel and control polymer groups were analyzed by a one-way ANOVA with a multiple comparison of means using Student's t-test. All statistical analyses were performed using the statistical program SAS JMP (SAS Institute, Cary, N.C.). Values of $p<0.05$ were considered statistically significant for all tests.

Results and Discussion

In Vitro NO Release from Films Containing $DBHD/N_2O_2$ in PVC/DOS with PLGA Additives The diazeniumdiolate species investigated here, $DBHD/N_2O_2$, decomposes to generate NO primarily by a proton-driven mechanism. Tetrakis-(p-chlorophenyl)-borate derivative was previously used as a lipophilic additive counterion to stabilize the pH within NO releasing polymers prepared with $DBHD/N_2O_2$ previously. However, the borate derivative may not be an ideal additive because of its potential toxicity. In examples of the present disclosure, PLGA additives with varying hydrolysis rates were used as a replacement to the borate derivative to act as a proton donor source to control the NO release from $DBHD/N_2O_2$-doped PVC coatings. In the presence of water, the ester bonds in PLGA hydrolyze to yield lactic acid and glycolic acid, and PLGA is a widely used biodegradable/biocompatible polymer that has been approved by the FDA for numerous products.

The films used in this study had a three layer configuration: base coat, active coat, and top coat. The base and top-coat consisted of PVC/DOS in a 2:1 ratio, and the active coat consisted of PVC/DOS with 25 wt % $DBHD/N_2O_2$ and 10 wt % PLGA additive. PVC films containing $DBHD/N_2O_2$ with a 2:1 ratio of PVC:DOS have a more prolonged NO release as compared to 1:1 or 1:2 ratio of PVC:DOS. Therefore, in examples of the present disclosure, a 2:1 ratio of PVC:DOS was used. Top and base coats were employed for three main reasons: 1) to prevent leaching of $DBHD/N_2O_2$; 2) to neutralize the surface charge; and 3) to yield a smoother finish to the surface. In the present examples, 5050DLG1A (1-2 week hydrolysis rate) and 5050DLG7E/6535DLG7E (1-2 month/3-4 month hydrolysis rate) PLGAs were compared. These product names identify polymer mole ratio, polymer type, target IV designator and the end group designation (ester or acid). For example, 5050DLG7E stands for: 50 mole % DL-lactide, 50 mole % glycolide, 0.7 dL/g and 'E' for an ester end group (see Table 1 below). All the films were tested and stored at 37° C. in PBS buffer, which was changed every day.

TABLE 1

Analytical Info for the 5050DLG1A, 5050DLG7E, 6535DLG7E poly(lactide-co-glycolide) additives

| PLGA | Copolymer Ratio ($^1$H NMR) (Lactide:Glycolide)* | Acid number (mg KOH/g PLGA) | Inherent viscosity* (dL/g) | Molecular weight (GPC)* $M_w$ (kDa) | PDI |
|---|---|---|---|---|---|
| 5050DLG1A | 52:48 | 60.4 ± 2.5 | 0.08 | 4.1 | 2.1 |
| 5050DLG7E | 51:49 | 2.4 ± 0.8 | 0.65 | 106 | 1.6 |
| 6535DLG7E | 65:35 | 1.4 ± 0.5 | 0.78 | 121 | 1.6 |

Figure 2:
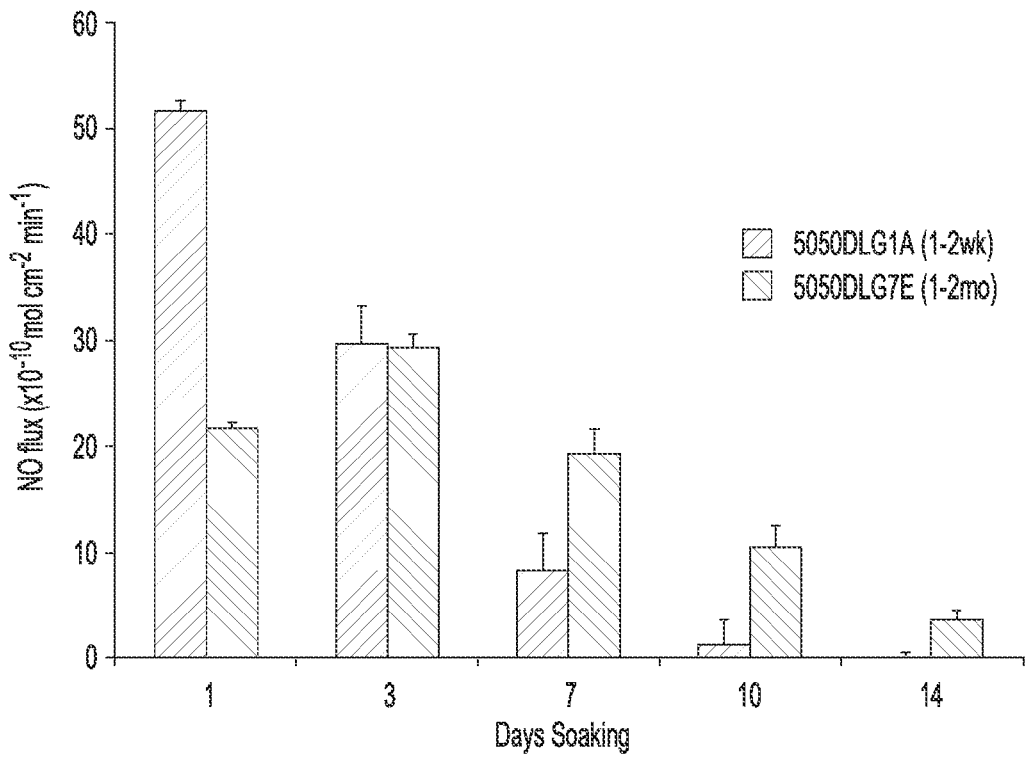
FIG. 2 shows NO release profiles of 25 wt % DBHD/$N_2O_2$ films containing 10 wt % 5050DLG1A (1-2 week) and 5050DLG7E (1-2 month) PLGA additives in PVC/DOS polymer matrix (the data are means±SEM)
Figure 2A:
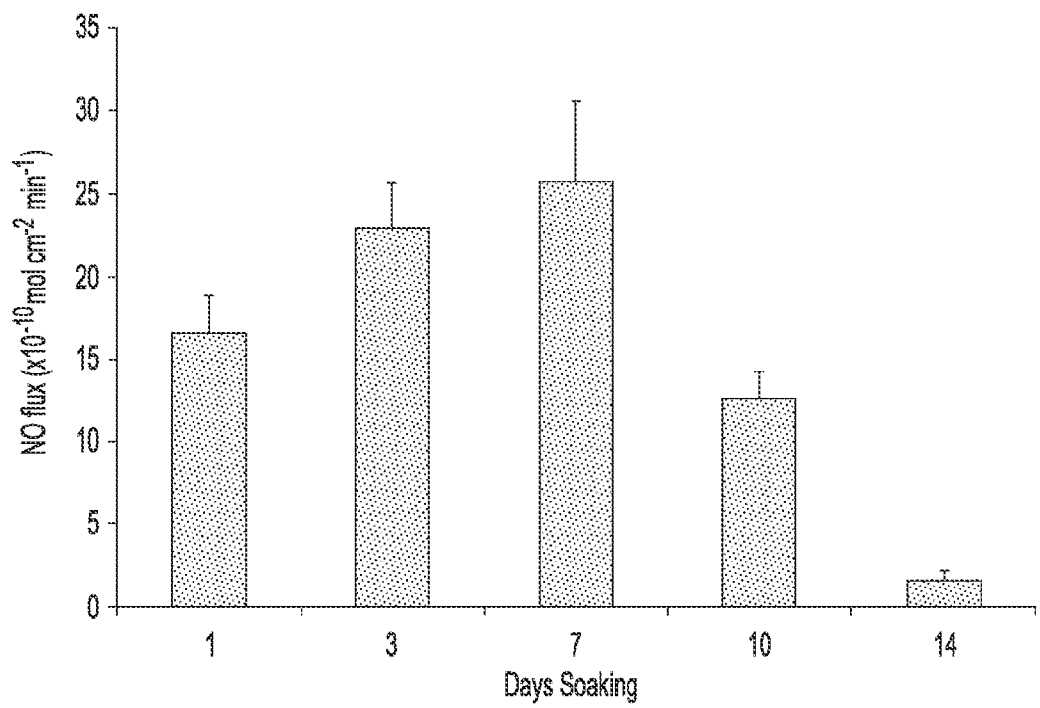
FIG. 2A shows an NO release profile of a 25 wt % DBHD/$N_2O_2$ film containing 10 wt % 6535DLG7E (1-2 month) PLGA additive in PVC/DOS polymer matrix (the data are means±SEM)

It has been previously reported that DBHD/N$_2$O$_2$ within PVC films without an additive releases NO, producing the corresponding diamine, DBHD, that raises the pH within the polymer film, thereby slowing and eventually stopping the NO release in 1-2 days. Use of a PLGA additive promotes a more sustained NO release. As shown in FIG. 2, DBHD/N$_2$O$_2$ with 5050DLG1A as the additive had an initial burst of NO due to high proton activity, but NO release quickly diminished over a 10 day period. In contrast, as shown in FIGS. 2 and 2A, the 5050DLG7E and 6535DLG7E additive films had a more constant NO flux with no initial burst of NO, and this allows the NO release to be prolonged for a 14 day period. Not only does the 5050DLG1A hydrolyze and produce acid monomers more quickly than either of the 5050DLG7E and 6535DLG7E, but it has a higher initial acid content (compared to the ester capped PLGA). The higher acid content and faster hydrolysis rate of the 5050DLG1A directly correlates to the high initial burst and greater early fluxes of NO observed, quickly depleting the DBHD/N$_2$O$_2$ reservoir.

Figure 3:
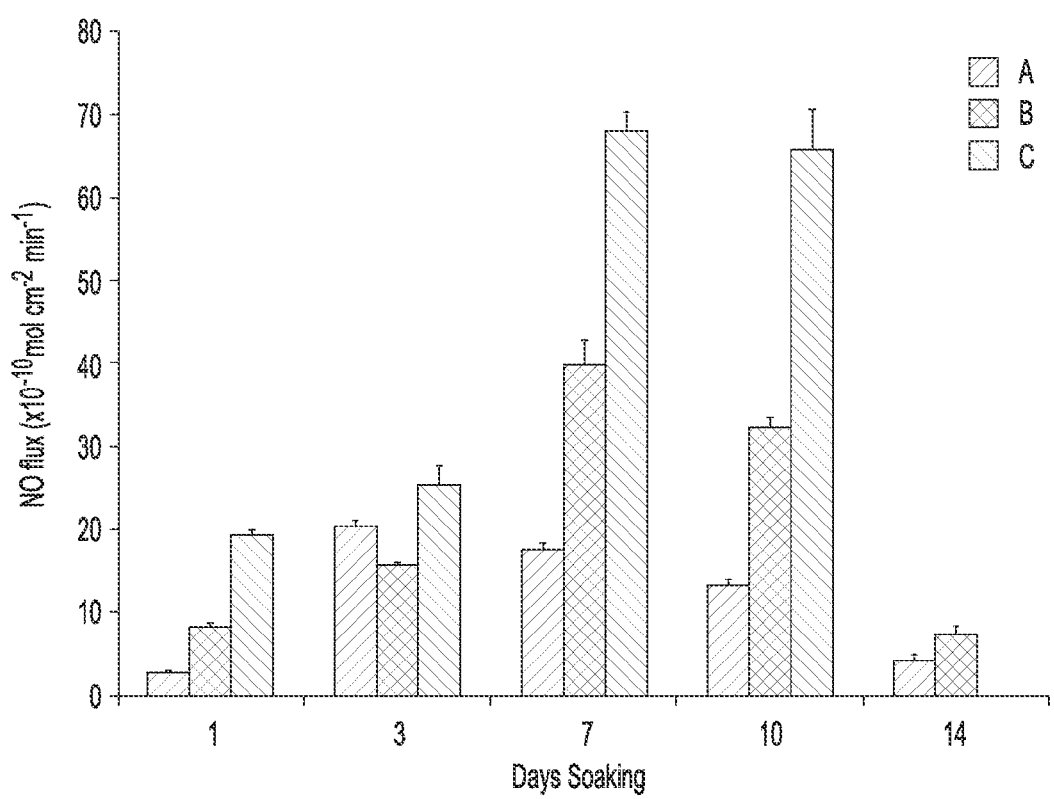
FIG. 3 shows NO release profiles of A) 5 wt % 5050DLG7E+25 wt % DBHD/$N_2O_2$; B) 10 wt % 5050DLG7E+35 wt % DBHD/$N_2O_2$; and C) 30 wt % 5050DLG7E+25 wt % DBHD/$N_2O_2$ films in PVC/DOS polymer matrix (the data are means±SEM)

As illustrated by FIGS. 2 and 2A, it was fortuitously found that the 5050DLG7E and 6535DLG7E additive films exhibit little or no initial burst of NO, but could advantageously release the NO for a prolonged time period. In order to study the film formulation containing 5050DLG7E, the amounts of PLGA (about 5 wt % to about 30 wt %) and DBHD/N$_2$O$_2$ (about 25% to about 35 wt %) were varied. The 5 wt % 5050DLG7E films released NO for 14 days; however the fluxes were relatively low (for example, $<4\times10^{-10}$ mol/cm$^2$-min). These low fluxes indicate that the 5 wt % PLGA was generally not adequate to compensate for the pH increase due to production of DBHD within the film. Increasing the 5050DLG7E to 30 wt % yielded films that exhibited high fluxes (for example, $>40\times10^{-10}$ mol/cm$^2$-min) from days 7-10 due to the increased amount of acid monomers being produced, resulting in complete depletion of the NO reservoir by day 14. Increasing the DBHD/N$_2$O$_2$ content of the films to 35 wt % yielded a lower initial NO flux, but overall did not show any significant improvement or prolong the NO release compared to the lower 25 wt % DBHD/N$_2$O$_2$ films. Based on data shown in FIG. 3, 25 wt % DBHD/N$_2$O$_2$ with 10 wt % 5050DLG7E was found to provide desirable sustained NO release, and hence was used for subsequent thrombosis evaluation in an ECC rabbit model in examples of the present disclosure.

Correlating NO Release and pH Change in the Films

At 37° C., incubation of DBHD/N$_2$O$_2$ films in PBS enables NO to be released through a proton driven mechanism, and the diamine DBHD product formed further increases the pH within the PVC film, causing the NO release to decrease and eventually cease completely, without all the NO delivered. In contrast, using ester capped PLGA as an additive in appropriate proportion helps ensure that DBHD/N$_2$O$_2$ is the limiting reagent and the entire NO payload is released. Ester capped PLGA continues to hydrolyze, thereby creating an acidic environment essential for sustained NO release. Hydrolysis of PLGA takes place simultaneously with NO release, balancing the pH of the film in a pH range that favors NO release. However, the present inventors have found that an important component to desirably sustaining the NO release from these formulations is balancing the rates of PLGA hydrolysis with the rate of DBHD amine production.

Figure 4A:
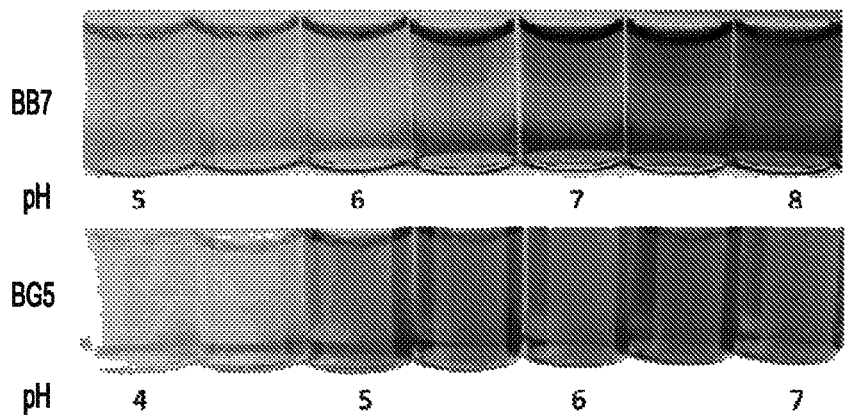
FIGS. 4A-4C show: a comparison of color changes of bromocresol green (BG5) and bromothymol blue (BB7) in PBS buffer at various pH values (FIG. 4A); a comparison of color changes of BG5 and BB7 doped with 25 wt % DBHD/$N_2O_2$ and 10 wt % of 5050DLG1A PLGA in plasticized PVC polymer matrix (FIG. 4B); and a comparison of color changes of BG5 and BB7 doped with 25 wt % DBHD/$N_2O_2$ and 10 wt % of 5050DLG7E PLGA in plasticized PVC polymer matrix (FIG. 4C) (all films were incubated at 37° C. for 14 days in PBS buffer)

Further, the present inventors have found that studying the pH changes within the polymer matrix as a function of time provides a means to further support the hypothesis that the addition of ester capped PLGA to the PVC films derives its benefit via control of the polymer phase pH. Previously, Chromoionophore II (9-Dimethyl-amino-5-[4-(16-butyl-2,14-dioxo-3,15-dioxaeicosyl)phenylimino]benzo[a]phenoxazine) was doped into a PVC/DOS film with DBHD/N$_2$O$_2$; however, this method merely demonstrated the mechanism whereby this matrix becomes more basic over time without any detailed correlation to NO release rate. The pH within pure PLGA matrices has been studied previously using confocal microscopy with acidic pH sensitive probe Lysosensor yellow/blue. In the present disclosure, doping the films with pH indicator dyes provides a convenient and inexpensive way to optically/visualize the pH changes that occur throughout the 14 day incubation period. The amount of dye added to the films is important, as too little dye will prevent visual interpretation, while too much dye will compete with the DBHD/N$_2$O$_2$ reaction. As shown in FIG. 4A, bromothymol blue (BB7) has a pH transition range of 6-7, and bromocresol green (BG5) has a pH transition range of 4-5, where yellow is acidic and blue indicates basic conditions.

The DBHD/N$_2$O$_2$ only films doped with the pH indicator dyes initially showed a basic environment (all films were blue). This basic environment was maintained throughout the incubation time period. This demonstrates that without an additive, the pH in the DBHD/N$_2$O$_2$ only films remains basic (it is believed from free DBHD within the DBHD/N$_2$O$_2$ preparation) and prevents any further NO release. The dyes were also added to the PLGA+PVC/DOS films (without any DBHD/N$_2$O$_2$), and all showed an acidic environment (yellow color).

Figure 4B:
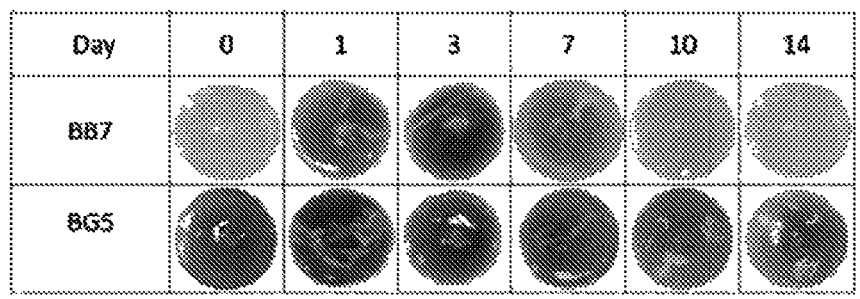

In contrast, the films doped with 5050DLG1A and 25 wt % DBHD/N$_2$O$_2$ released NO for 10 days, but had a burst of NO on the first day of soaking. As shown in FIG. 4B, the pH indicators in these 5050DLG1A doped films indicated an initially acidic environment (pH ~5-6). This initial acidic environment correlates to the observed large NO burst on day 1, which is believed to be caused by the high free acid content in the 5050DLG1A (see Table 1 above). After 1 day of soaking, the 5050DLG1A film doped with BB7 indicated an increase in pH (color changed from yellow to green). This increase of pH was caused by the high flux of NO that occurred (see FIG. 2), thereby producing significant amounts of the free DBHD amine within the film during a short period of time. By days 7-10, the NO flux had significantly diminished, during which time both dyes began to gradually indicate a decrease in pH (films turned green and then yellow), an indication that the DBHD/N$_2$O$_2$ reservoir had been depleted as the PLGA continued to hydrolyze, recreating an acidic environment (pH of about 5).

Figure 4C:
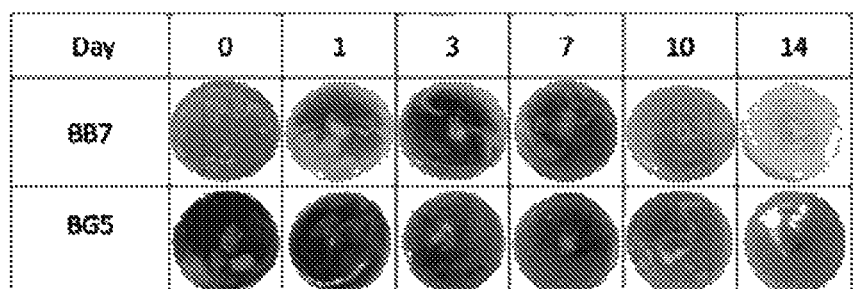

Additionally, as reported above, NO release profiles of the 5050DLG7E doped films showed a desirable balance between the hydrolysis rate of the ester capped PLGA and NO release from DBHD/N$_2$O$_2$, yielding a prolonged NO release. The pH indicators showed (see FIG. 4C) that these films also were initially acidic (pH of about 6-7), but less acidic than the 5050DLG1A films. In fact, the 5050DLG7E polymer has a much lower acid content and slower hydrolysis rate in comparison to the 5050DLG1A polymer; therefore, no initial burst of NO was observed with either the 5050DLG7E polymer or the 6535DLG7E polymer. This lower initial acid content is believed to be important to prolonging the NO release from these films. The films containing 5050DLG7E PLGA exhibited little color change until day 10-14, when they began to become more acidic. This demonstrates that the acid production rate (from the ester capped PLGA hydrolysis) and DBHD amine production rate is likely closely balanced within these films. Without being bound to any theory, it is believed that this explains the consistency of the pH and NO release from day to day with the examples of the films of the present disclosure including examples of the ester capped PLGA. These films also turned yellow by day 14, indicating the depletion of the NO reservoir. In short, the use of pH indicators within the films provides further evidence that the 5050DLG7E and 6535 DLG7E PLGA hydrolysis rate balances the decomposition rate of the DBHD/$N_2O_2$, producing a desirable pH and concomitant NO flux profile.

PLGA Doped NOrel Films in ECC and Effects on Rabbit Hemodynamics

Figure 5:
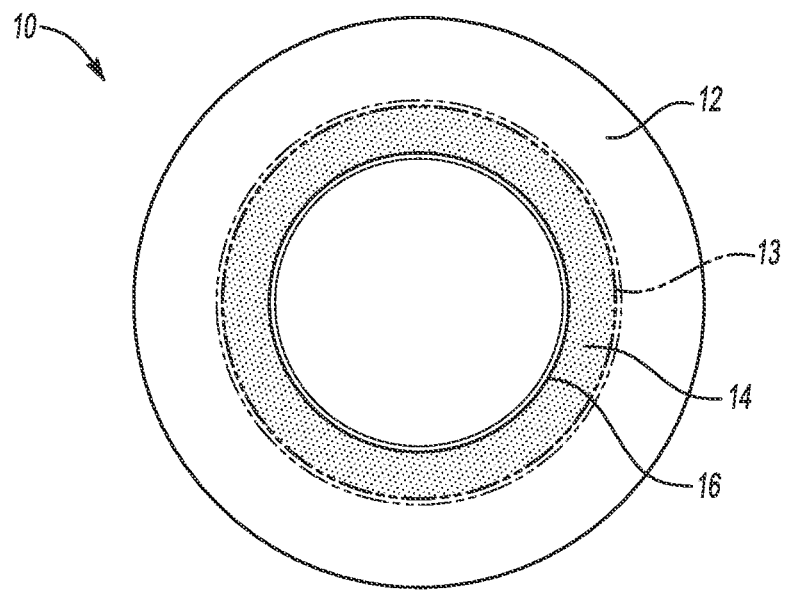
FIG. 5 is a schematic view of an ECC loop tubing coated with a base coat (shown in phantom) of 100% PVC (limiting NO diffusion into the TYGON® tubing); an active coat containing plasticized PVC doped with lipophilic DBHD/$N_2O_2$ and PLGA additive (or Elast-eon E2As doped with lipophilic DBHD/$N_2O_2$ and PLGA additive); and a top coat of plasticized PVC (or Elast-eon E2As) over the active coat providing a smooth surface and limiting the NO release over a 4 hour in vivo rabbit study.

ECC circuits are shown schematically at reference numeral 10 in FIG. 5. The ECC circuit 10 is formed from a suitable polymer tubing 12 (such as, e.g., Tygon™ PVC tubing). The tubing 12 in some examples includes coated thereon a base coat 13 formed from 100% polymer (such as, e.g., PVC). The circuit 10 includes an active coat 14 on the base coat 13 (if included) or on the interior wall of the tubing 12 (if no base coat 13 is included). The circuit 10 further includes a top coat 16 disposed on the active coat 14.

In a first example, the ECC circuit 10 includes PVC tubing 12, a base coat 13 formed from 100% PVC, an active coat 14 formed from 65 wt % 2:1 PVC/DOS, 25 wt % DBHD/$N_2O_2$ and 10 wt % 5050DLG7E PLGA, and a top coat 16 formed from 1:2 PVC/DOS.

In a second example, the ECC circuit 10 includes PVC tubing 12, an active coat 14 on the tubing 12, the active coat 14 formed from 65 wt % Elast-eon E2As polymer, 25 wt % DBHD/$N_2O_2$ and 10 wt % 5050DLG7E PLGA, and a top coat 16 formed from Elast-eon E2As polymer.

The ECC circuits 10 coated (as schematically shown in FIG. 5) with PVC containing the 5050DLG7E PLGA/DBHD/$N_2O_2$ NO release formulation (according to the first example) were tested for NO release flux, pre-rabbit surgery and post-4 hour rabbit surgery. The PVC coating material (containing ester capped PLGA) continuously releases NO under physiological conditions at levels that exceed the physiological NO release level from endothelial cells ($0.5 \times 10^{-10}$ mol cm$^{-2}$ min$^{-1}$ to $4 \times 10^{-10}$ mol cm$^{-2}$ min$^{-1}$). The NO release as measured using a chemiluminescence NO analyzer showed a sustained NO flux of approximately $11 \times 10^{-10}$ mol cm$^{-2}$ min$^{-1}$ for 4 hours (the ECC coatings are generally not very thick because the purpose is to survive only 4 hours). The NO release from the ECC circuit did not decrease significantly when exposed to the flowing blood. Indeed, after 4 hours of blood flow, the NO flux was found to be $10 \times 10^{-10}$ mol cm$^{-2}$ min$^{-1}$ post-surgery. The fact that the blood environment does not alter the kinetics of the NO release from the coating is supported by this data.

The ECC blood flow was maintained at approximately 105 mL/min for the NOrel circuits over the 4 hour test period. However, the blood flow dropped from the initial 105 mL/min to approximately 80 mL/min in the first one hour for the control circuits, and then was maintained at 80 mL/min for the remainder of the 4 hour period. This maintenance of blood flow in the control circuits is due to the addition of intravascular fluids to the animal over the test period. No significant difference in the mean arterial pressure of the animals on the NOrel vs. control circuits was noted, with pressures averaging 46±4 mmHg for both types of circuits. The activation clotting time for blood obtained from the test animals increased over the 4 hour period for both NOrel and control coated circuits. As noted in previous studies, this behavior can be attributed to the increase in intravascular fluids and concomitant hemodilution effect.

Figure 6:
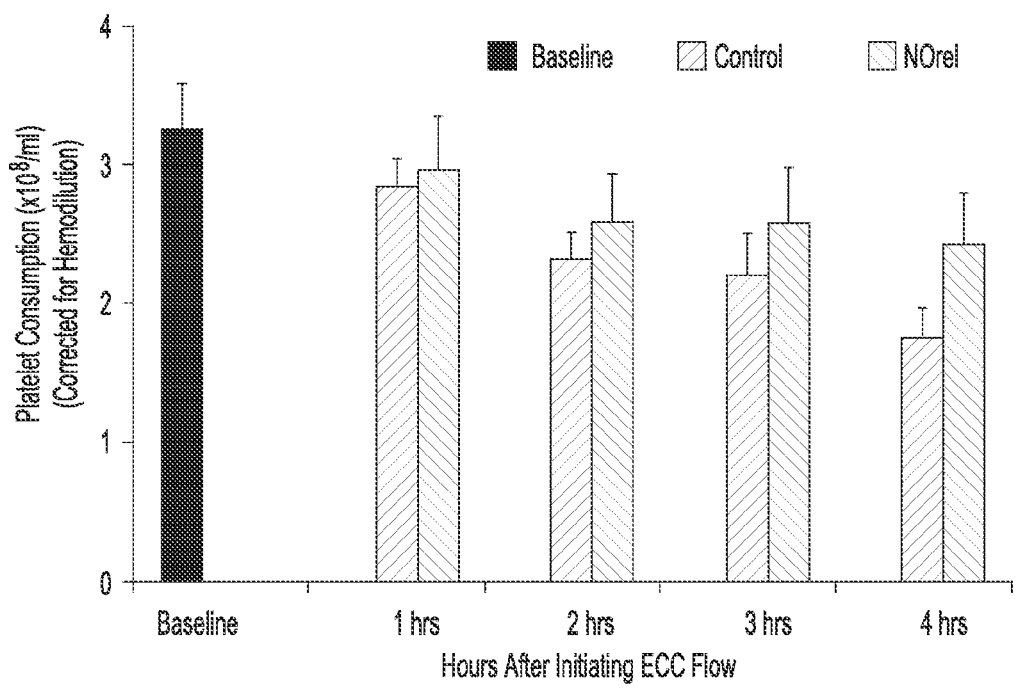
FIG. 6 depicts time dependent effects on rabbit platelet counts (as % consumption) of 25 wt % DBHD/$N_2O_2$+10 wt % PLGA (in plasticized PVC coating) during 4 hour ECC as measured via Coulter counter (the data are means±SEM)

Effects of PLGA Doped NOrel PVC Polymer Coatings on Rabbit Platelet Function, Fibrinogen Levels and Thrombus Formation Platelet function during exposure to the NOrel and control polymer-coated ECCs was assessed by observing platelet count (see FIG. 6) and percent of platelet aggregation, as determined by ex-vivo collagen (40 µg/mL) stimulation of PRP. Platelet count was corrected for any hemodilution due to added IV fluids into the rabbits. Four out of 7 control circuits were clotted within 3 hours, whereas all the NOrel coated circuits were patent after 4 hours. The animals run with the NOrel polymer coated ECCs showed 79±11% preservation of the platelet count over the course of the 4 hour blood contact period, whereas animals equipped with the control polymer ECCs showed a time-dependent loss in platelet count. By the end of the 4 hour period only, 54±6% platelet count was preserved for this group of rabbits. Both NOrel and control coated ECC showed similar response to collagen-stimulated platelet aggregation over the course of 4 hour blood exposure. The percent of platelet functional aggregation was determined by ex-vivo collagen stimulation of PRP, measured by optical turbidity. NOrel and control coated circuits were able to maintain 88% and 91% aggregation, respectively, compared to their baseline values.

Figure 7A:
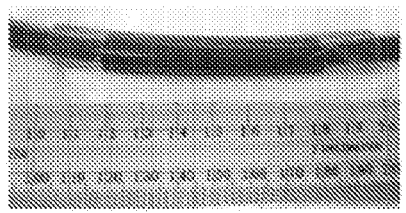
FIGS. 7A-7C show evaluation of thrombus formation on NOrel and a control polymer ECC after 4 hours of blood exposure in a rabbit thrombogenicity model.
Figure 7B:
Figure 7C:
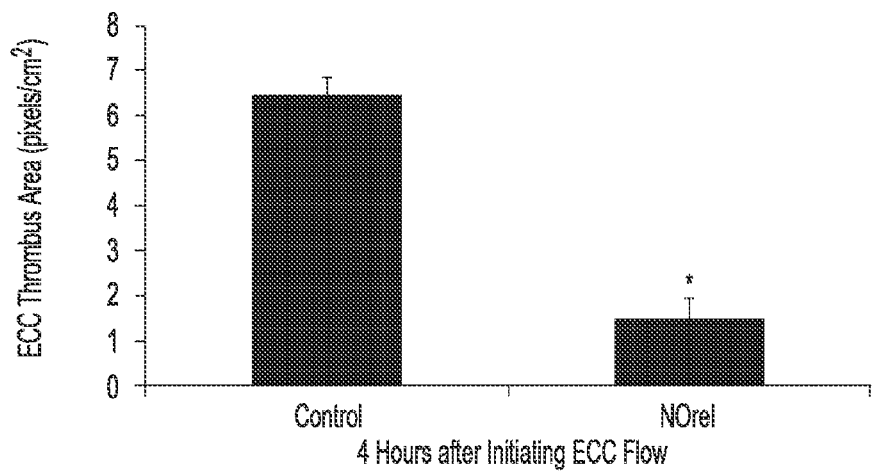

To ascertain the differential formation of thrombus in the thrombogenicity chamber (i.e., the ⅜ inch ID Tygon® tubing 8 cm in length within the ECC loop) of the NOrel vs. control polymer-coated ECCs, 2-dimensional (2D) image analysis was performed after 4 hours of blood exposure. FIGS. 7A and 7B show representative images of the control and NORel circuits, respectively, after being run for 4 hours in the rabbit ECC model. The threshold feature in the Image J imaging software was used to calculate a 2D area of thrombus formation (pixels/cm$^2$) in each tubing chamber. These thrombi area measurements were quantitated and, as shown in FIG. 7C, the thrombus area of the NOrel polymer ECC was significantly reduced compared to the control polymer ECCs, 1.5±0.5 and 6.5±0.4 pixels/cm$^2$, respectively.

Figure 8:
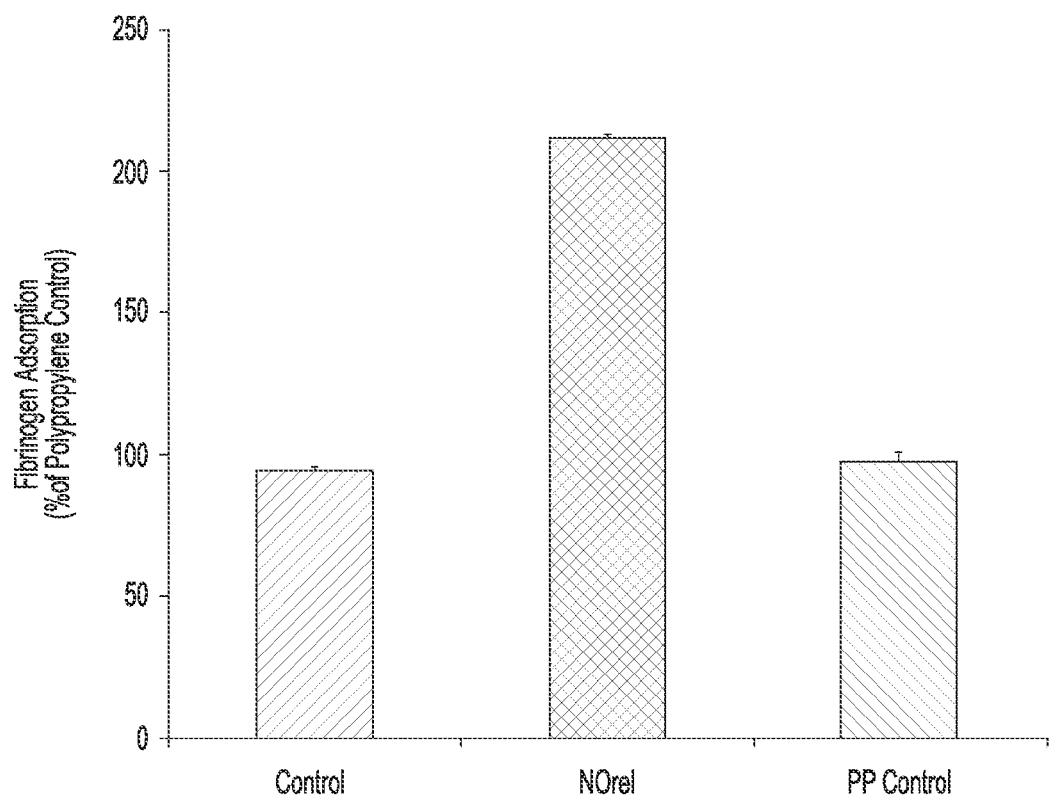
FIG. 8 shows an in vitro fibrinogen adsorption assay on NOrel (25 wt % DBHD/$N_2O_2$+10 wt % 5050DLG7E PLGA in PVC/DOS) and a control (10 wt % 5050DLG7E PLGA in PVC/DOS) polymers, the fluorescence assay in a 96-well format that used a goat antihuman fibrinogen-FITC conjugated antibody to measure the level of adsorbed human fibrinogen (3 mg/mL) to plated NOrel and control polymers (the data are means±SEM)

An in vitro immunofluorescence assay was performed to determine if plasma protein adsorption, especially, human fibrinogen, occurs on the surface of the two different polymer coatings. As shown in FIG. 8, the PLGA doped NOrel PVC coating exhibited significant fibrinogen adsorption, with a value of 211±1.5% of the 3000 µg/mL fibrinogen control (n=8), compared to the control (PLGA/PVC-DOS) polymer's 133±16% of the 3000 µg/mL fibrinogen control (n=8). The adsorption of the human fibrinogen antibody without the presence of exogenous human fibrinogen was 100±1.6% of the 3000 µg/mL fibrinogen control. The adsorption of human fibrinogen on the PLGA doped NOrel PVC coating is significantly (10 times) lower than the reported value for tetrakis-(p-chlorophenyl)-borate doped NOrel coatings. The lower amount of fibrinogen adsorption on PLGA doped NOrel PVC coatings make these coatings more favorable for hemocompatible applications.

Figure 9:
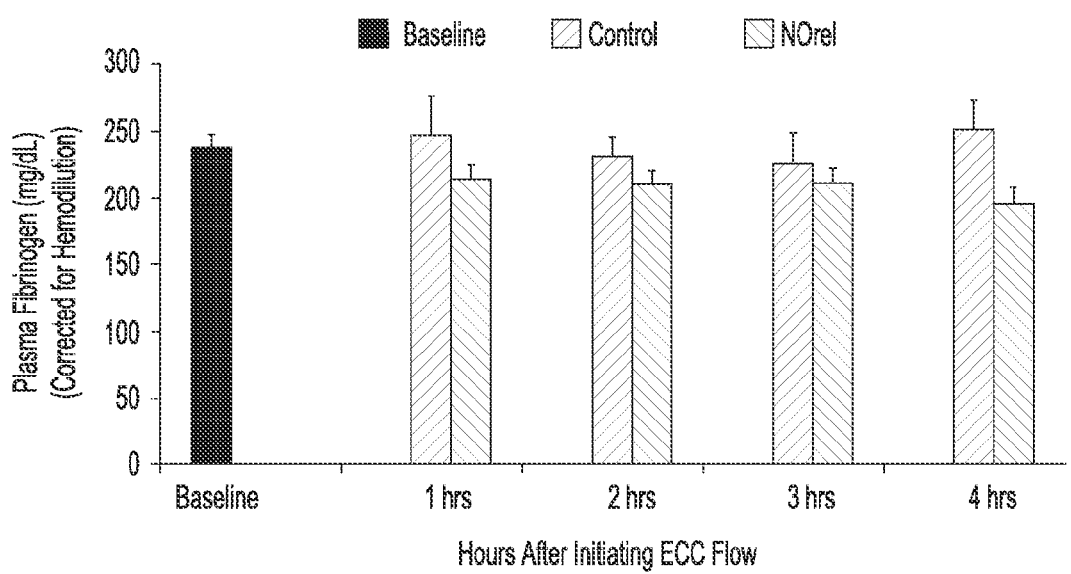
FIG. 9 shows time-dependent effects of NOrel and control ECC loops on plasma fibrinogen levels during 4 hours of blood exposure in a rabbit thrombogenicity study (the data are means±SEM)

The level of plasma fibrinogen to which the activated platelets bind during the 4 hour ECC blood exposure was also assessed. The plasma fibrinogen levels were corrected for any hemodilution due to added IV fluids into the rabbits. FIG. 9 illustrates that the plasma fibrinogen levels significantly decrease in both the NOrel and control ECCs in a time-dependent manner. There was not much difference between the present example NOrel polymers and the control polymers in their ability to bind fibrinogen at any time point. The decrease in plasma fibrinogen levels can be attributed to binding of the fibrinogen to the ECC surfaces, as shown clearly by the in vitro immunofluorescence assay data (see FIG. 8 above).

Long-Term Catheter Implantation in Rabbit Model

Rabbit Catheter Implantation Protocol:

All animals were cared for by the standards of the University Committee on Use and Care of Animals (UCUCA) at the University of Michigan. The surgical area was sanitized and dedicated to the purpose of performing surgery. All surgical instruments were sterilized using steam sterilization and sterile drapes were used to create a sterile field around the dorsal and ventral sides of rabbit neck. A total of 6 New Zealand white rabbits (Myrtle's Rabbitry, Thompson's Station, Tenn.) were used in this study. All rabbits (2.5-3.5 kg) were initially anesthetized with intramuscular injections of 5 mg/kg xylazine injectable (AnaSed® Lloyd Laboratories Shenandoah, Iowa) and 30 mg/kg ketamine hydrochloride (Hospira, Inc. Lake Forest, Ill.). Maintenance anesthesia was administered via isoflurane gas inhalation at a rate of 1.5-3% via mechanical ventilation which was done via a tracheotomy and using an A.D.S. 2000 Ventilator (Engler Engineering Corp. Hialeah, Fla.). The rabbit neck area was cleaned with iodine and ethanol prior to incision. A modified rabbit venous model, originally developed by Klement et al, was used where the facial vein was used as an access point to the external jugular vein, and the tip of the catheter was placed at the entrance to the right atrium. By using the facial vein, the external jugular vein blood flow was maintained over the catheter which provided both thrombosis and biofilm assessments. Under sterile conditions, a small skin incision (2 cm) was made over the right external jugular vein and the internal jugular vein branch isolated for the catheter insertion. Briefly, the internal jugular vein was ligated proximally and under distal occlusion, a small venotomy was made through which the catheter was introduced into the jugular vein through the facial vein and then advanced into the cranial vena cava, as shown in FIG. 10.

Figure 10:
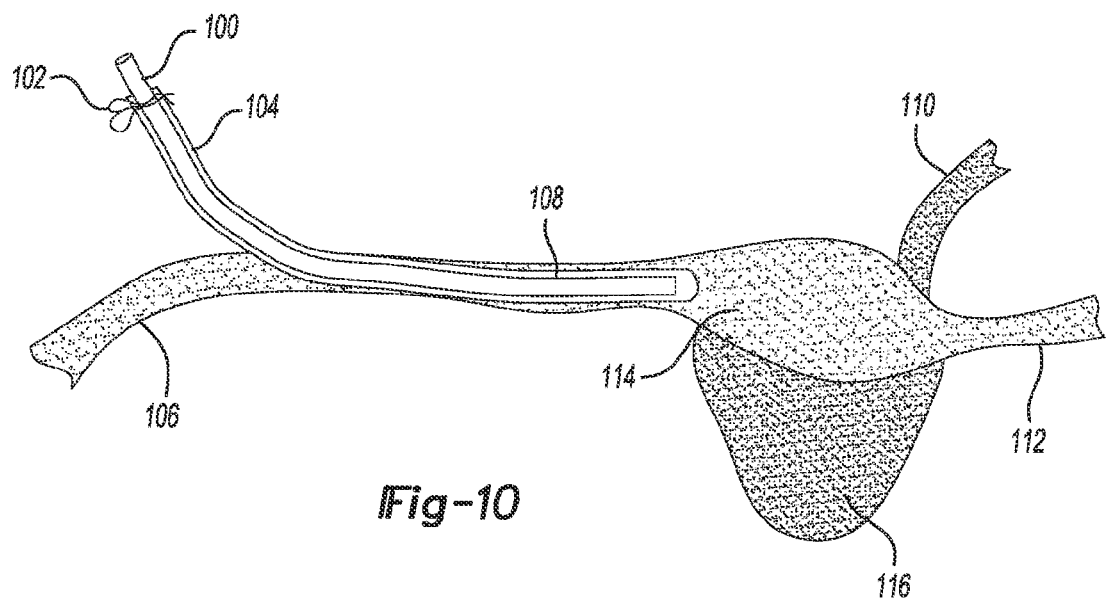
FIG. 10 is a schematic illustration of catheter placement in a conscious rabbit model.

FIG. 10 shows the NOrel or control catheter at reference numeral 100. The ligation is shown at 102. The facial vein is shown at 104; the external jugular vein at 106; the cranial vena cava at 108; the pulmonary artery at 110; the caudal vena cava at 112; the right atrium at 114; and the right ventricle at 116.

About 7 cm of a catheter length was inserted and then fixed to the vein at its entrance by two sterile silk sutures. A second skin incision (1 cm) was made on the dorsum of the neck. The remaining external portion (8 cm in length) of the catheter was then tunneled under the skin from the jugular vein entrance and was exteriorized through the dorsal skin incision. Skin incisions were closed in a routine manner using uninterrupted stitches (absorbable suture) for the ventral incision and interrupted stitches (absorbable suture) for the dorsal incision. The open end of the catheter was closed by a subcutaneous vascular access port. Thereafter, the incision sites were treated with Neosporin® ointment. Animals were given prophylactically Enrofloxacin (5 mg/kg SC daily for 4 days) as a broad spectrum antibiotic postoperatively. After removal from anesthesia, animals were placed in an oxygenated and 37° C. incubator for postoperative recovery. Animals were checked during 1-2 hour recovery until they were able to maintain sternal recumbency before moving to the animal facility.

Post-Operative Recovery Protocol:

The rabbits recovered from anesthesia after the catheter placements were housed individually with a respective cage card identifying the animal in the animal facility. Animal health was monitored during routine daily check-ups and weighing, the implanted venous catheter's exit site and the skin incision was examined for inflammation (redness). 4 mg/kg Rimadyl (analgesic) was given for 2 days after surgery and 5 mg/kg Baytril (antibiotic) was given for 4 days post-surgery. Two mL sterile saline was used to flush the catheter every day. After 9 days, rabbits were given 400 IU/kg sodium heparin just prior to euthanasia to prevent necrotic thrombosis. The animals were euthanized using a dose of Fatal Plus (130 mg/kg sodium pentobarbital) (Vortech Pharmaceuticals Dearborn, Mich.).

Catheter Evaluation:

After explanting, the catheters were rinsed in PBS. Pictures were taken of the exterior of the whole catheter and the interior of a 1 cm piece cut longitudinally using a Nikon L24 digital camera. Starting at the distal tip of the catheter, 1 cm sections were cut SEM, bacterial adhesion, and NO release testing. To quantitate the viable bacteria, a 1 cm piece was cut longitudinally and was homogenized in 1 mL PBS buffer. The optimal homogenizing speed was found using a separate experiment where different homogenizing speeds and times were compared. The resulting homogenate was serially diluted in sterile PBS. Triplicate aliquots of each dilution (10 μL) were plated on agar plates. The agar plates were incubated at 37° C. for 24 hours, followed by calculation of colony forming units per catheter surface area ($CFU/cm^2$).

Scanning Electron Microscopy

After explanation, 1 cm catheter pieces were immersed in 2.5% glutaraldehyde solution for 2 hours followed by 3 washes with phosphate buffer. Catheter pieces were treated with 1% Osmium tetroxide in 0.1M Cacodylate, pH 7.4 for 1 hour followed by 3 washes with phosphate buffer. The catheter samples were dehydrated in ascending series of ethyl alcohols (30%-100%), mounted on SEM stubs, and subsequently sputtered with gold. The specimens were examined in a scanning electron microscope AMRAY FE 1900(FEI Company, PHILIPS, Eindhoven, Netherlands) operating at 20 kV.

Further Results and Discussion

Comparison of Hemodynamic Effects of Four Biomedical Grade Polymers in ECC Rabbit Model The hemocompatibility of four biomedical grade polymers (Tecophillic SP-60D-60, Tecoflex SG80A, Elast-eon E2As, poly(vinyl chloride) (PVC)) was compared using a 4 hour rabbit thrombogenicity model. The goal of this comparison was to choose the polymer with the best hemocompatible properties to be combined with the novel NO release coatings disclosed herein for long-term implantation in rabbits. Based on the platelet count and clot area, the E2As polymer has superior intrinsic hemocompatible properties. The preservation of platelet count and reduced clot area may be attributed to the fact that the E2As polymer binds to albumin more strongly than fibrinogen (responsible for platelet activation and adhesion), and possibly pacifying the surface. However, it is to be understood that any suitable biocompatible polymer is contemplated for use in accordance with examples of the present disclosure, and the present inventors do not intend to limit the polymer to E2As. E2As is one example of a suitable biocompatible polymer. In Vitro NO Release from Catheters Containing DBHD/$N_2O_2$ in E2As with Various PLGA Additives The diazeniumdiolate species investigated here, DBHD/$N_2O_2$, decomposes to generate NO primarily by a proton-driven mechanism. Herein, we compare the NO release profiles from the 4 base polymers doped with DBHD/$N_2O_2$ and PLGA additives. We have previously demonstrated that acid capped PLGA gives a huge burst of NO on day 1, and then NO release lasts only 1 week. In the present disclosure, two different ester capped PLGA additives were used as a proton donor source to DBHD/$N_2O_2$-doped polymer coatings to maintain the pH for prolonging the release for a 2 week period. In the presence of water, the ester bonds in PLGA hydrolyze to yield lactic and glycolic acids, and PLGA is a widely used biodegradable/biocompatible polymer that has been approved by the U.S. Food and Drug Administration (FDA) for numerous products.

The NOrel films used in this study had an active NOrel layer that was topcoated with the corresponding base polymer, as described above. The active coat consisted of the base polymer doped with 25 wt % DBHD/$N_2O_2$ and 5 wt %, 10 wt %, or 25 wt % PLGA additive. The present inventors have found that twenty-five wt % DBHD/$N_2O_2$ is an optimum amount. It has been previously reported that DBHD/$N_2O_2$ within polymer films without an additive releases NO, producing the corresponding diamine, DBHD, that raises the pH within the polymer film, thereby slowing and eventually stopping the NO release in 1 to 2 days. As disclosed herein, use of a PLGA additive promotes a more sustained NO release.

The topcoat was employed for three main reasons: 1) to prevent leaching of DBHD/$N_2O_2$; 2) to neutralize the surface charge; and 3) to yield a smoother finish to the surface. In this study, 5050DLG7E (1-2 month hydrolysis rate) and 6535DLG7E (3-4 month hydrolysis rate) PLGAs were compared. We have already shown previously that higher acid content and faster hydrolysis rate of the 5050DLG1A (1-2 week hydrolysis rate) causes the high initial burst and greater initial NO fluxes which quickly depletes the DBHD/$N_2O_2$ reservoir. These product names identify polymer mole ratio, polymer type, target IV designator and the end group designation (ester or acid). For example, 5050DLG7E stands for: 50 mole % DL-lactide, 50 mole % glycolide, 0.7 dL/g and 'E' for an ester end group. All the films were tested and stored at 37° C. in PBS buffer, which was changed every day.

Figure 11:
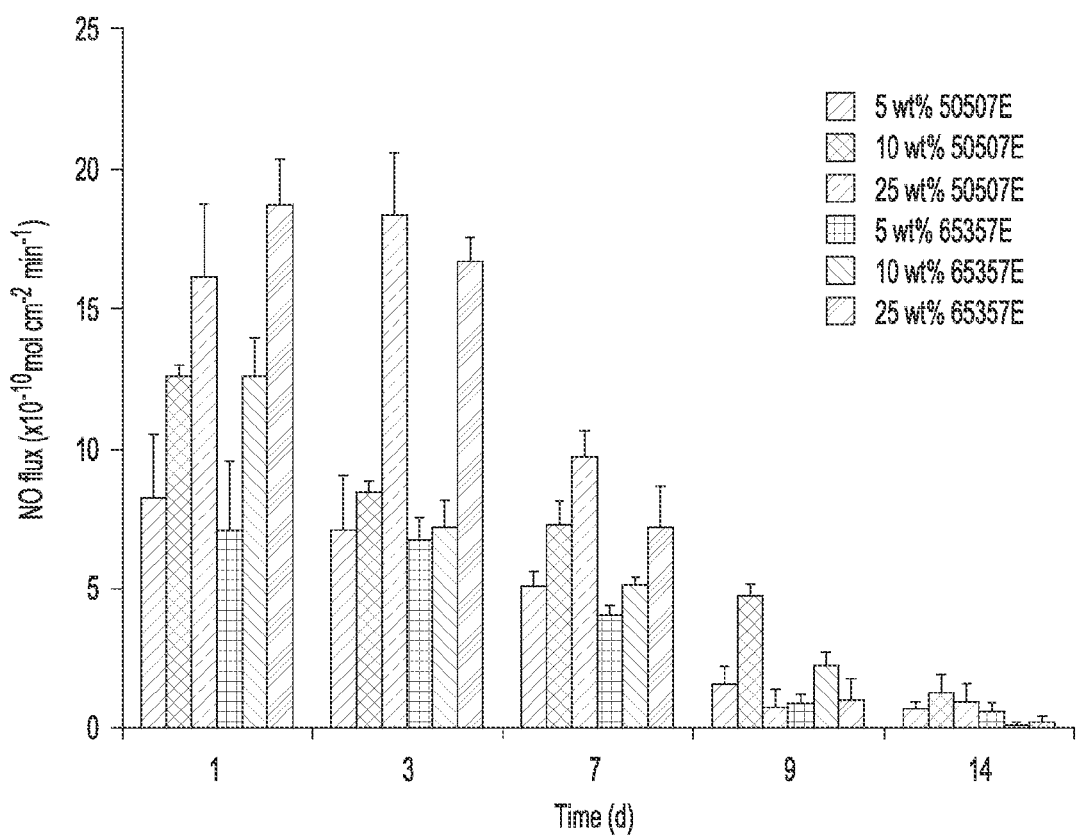
FIG. 11 shows NO release profiles of E2As polymer doped with 25 wt % DBHD/$N_2O_2$ and 5, 10, or 25 wt % 5050DLG7E PLGA or 6535DLG7E PLGA (the data are means±SEM)

FIG. 11 shows the complete NO release fluxes over a 2 week period for 25 wt % DBHD/$N_2O_2$ with 5, 10, and 25 wt % of 5050DLG7E and 6535DLG7E additives in E2As polymer. Elast-Eon™ E2As is a thermoplastic polyurethane elastomer with poly(dimethylsiloxane) (PDMS) soft segments commercially available from Aortech Biomaterials, Scoresby Victoria, Australia. E2As is a solution grade of E2A. E2As is one example of suitable siloxane-based polyurethane elastomers contemplated as being within the purview of the present disclosure. In FIG. 11, 5 wt % 5050DLG7E and 6535DLG7E films are shown to release NO for 14 days, however, the fluxes were quite low. These low fluxes indicate that the 5 wt % PLGA is not adequate to compensate for the pH increase due to production of DBHD within the film. Increasing the PLGAs to 25 wt % yields films that exhibit high fluxes on days 1-3 due to the increased amount of acid monomers being produced, resulting in complete depletion of the NO reservoir by day 14 with lower fluxes (<1) on days 9-14. There was no significant difference between the films containing the 5050DLG7E and 6535DLG7E PLGA additives. It is believed that this similarity may be attributed to the fact that the films were tested for the initial 2 week period, whereas these PLGAs have much longer hydrolysis timeframes. In addition, these PLGAs are being doped into hydrophobic polymers (with water uptake <8%), which likely slows the hydrolysis rates even further. Similar NO release profiles were observed for SG80A and PVC/DOS as compared to E2As, due to the similar water uptake properties. The films prepared with SP-60D-60 had a huge burst and higher fluxes initially, which dropped to less than $2 \times 10^{-10}$ mol cm$^{-2}$ min$^{-1}$ by day 9, likely due to the high water uptake (~60%). The films prepared with the 5050DLG7E additive had a more consistent NO flux with no initial burst of NO, and this enabled the NO release to be prolonged for a 14 day period with NO flux $>4 \times 10^{-10}$ mol cm$^{-2}$ min$^{-1}$ on day 9, and hence this formulation was used for subsequent short-term ECC and long-term catheter evaluations in rabbit models as disclosed herein.

Figure 12:
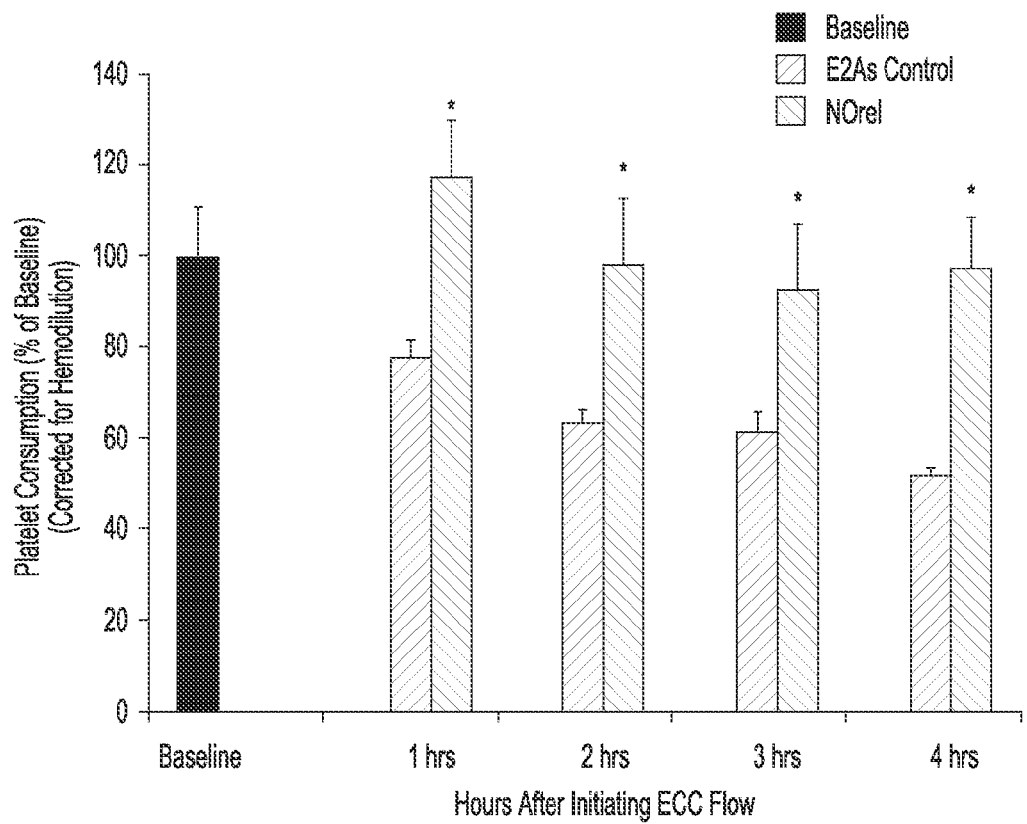
FIG. 12 shows time dependent effects of NOrel ECC (25 wt % DBHD/$N_2O_2$+10 wt % 5050DLG7E PLGA in E2As) as compared to control ECC on rabbit platelet count (i.e. consumption) as measured via Coulter counter (the data are means±SEM, *=p<0.05, control vs. NOrel ECC circuits)
Figure 13:
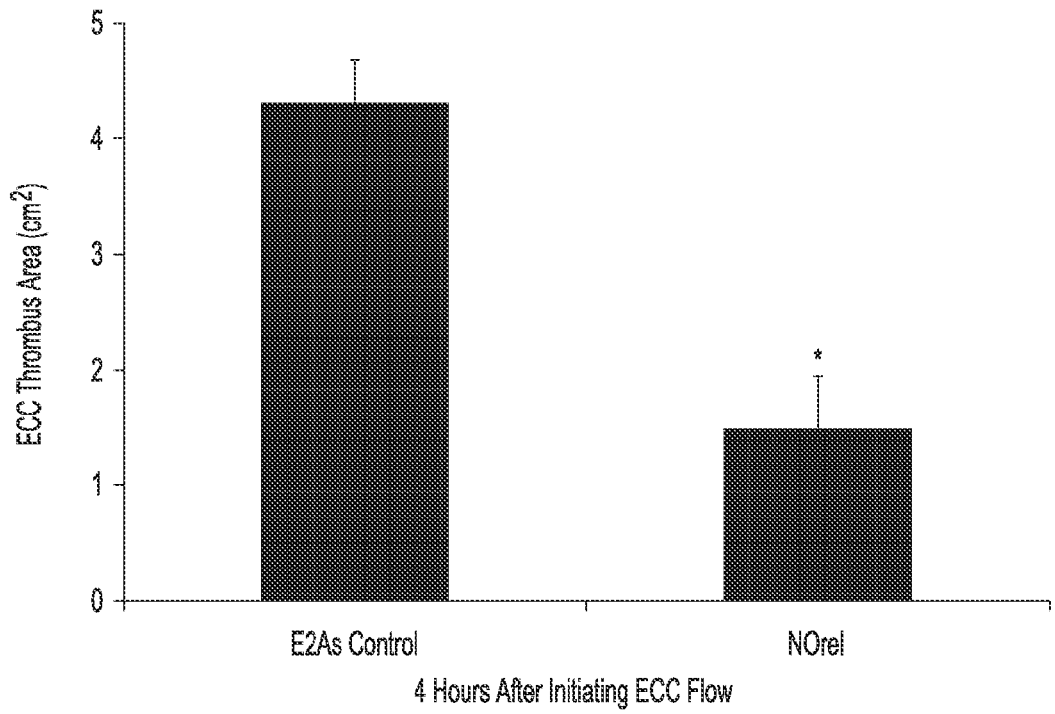
FIG. 13 shows quantitation of thrombus area as calculated with NIH ImageJ software using a 2D representation of thrombus (the data are means±SEM, *=p<0.05, control vs. NOrel ECC circuits)

Effects of E2As-Based NOrel Coating on Rabbit Platelet Function and Thrombus Formation in a Short Term (4 Hour) Application Prior to testing the E2As-based NOrel coating for long term effects, a short-term 4 hour rabbit ECC model was used to observe their effects on platelet count, platelet function, and clotting. As described above, platelet activation and function throughout the 4 hour ECC was assessed by recording the platelet count and platelet aggregation, which were both corrected for hemodilution due to the added IV fluids. For NOrel, all 5 ECC loops survived the 4 hour experiment, whereas for E2As control 4 out of 5 loops survived the 4 hour ECC run. For the NOrel circuits, the platelet count initially rose slightly and was maintained at 97±11% of baseline levels at the end of the 4 hour ECC. The platelet count for E2As control circuits observed a time-dependent loss in platelets dropping to 58±3% of baseline after 4 hours (FIG. 12). Image J software was used to quantify the clot area in each thrombogenicity chamber. As show in FIG. 13, a significant reduction of clot area was observed on NOrel as compared to E2As controls, 1.5±0.5 and 6.5±0.4 pixels/cm$^2$, respectively.

The blood from animals subjected to the NOrel and control ECCs exhibited similar response to collagen-stimulated platelet aggregation over the course of 4 hour blood exposure. The percent of platelet aggregation was determined by ex-vivo collagen stimulation of PRP, measured by optical turbidity. The ability to aggregate upon exogenous collagen stimulation was maintained with NOrel ECCs at 91% after 4 hours, whereas the platelets from control ECCs had only 49% ability to aggregate, compared to baseline values. NOrel materials have the ability to preserve platelet function and ability to aggregate.

The E2As-based NOrel ECC circuits 10 (as schematically shown in FIG. 5, and according to the second example described above) were tested for NO release, pre- and post-4 hour rabbit blood exposure. The NO release as measured using chemiluminescence NO analyzer shows a sustained NO flux of approximately $6 \times 10^{-10}$ mol cm$^{-2}$ min$^{-1}$ for 4 hours. After 4 hours of exposure to flowing blood, the ECC loops still exhibit a flux of $5.5 \times 10^{-10}$ mol cm$^{-2}$ min$^{-1}$. Due to the encouraging results of E2As based NOrel coatings in the short-term application, the NOrel material was tested in a long-term catheter model as described herein.

Figure 5A:
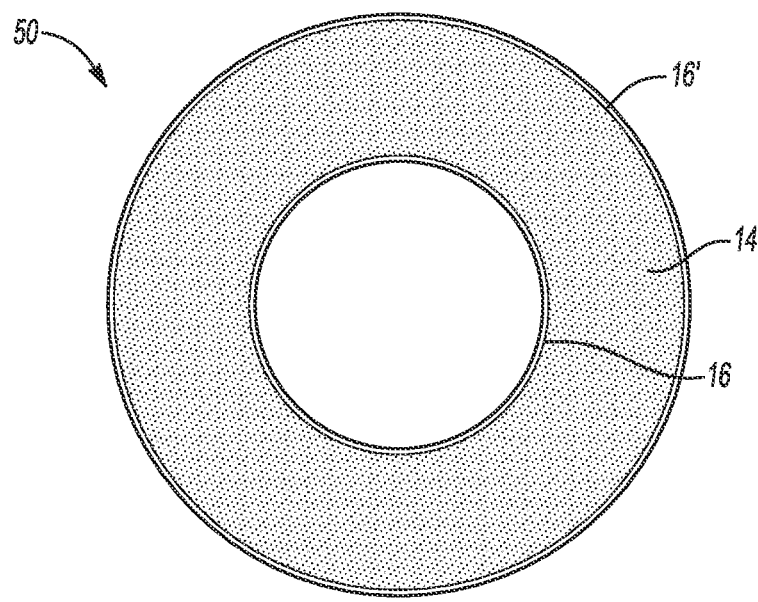
FIG. 5A is a schematic view of an intravascular E2As catheter doped with a lipophilic DBHD/$N_2O_2$ and the PLGA additive, between top coats of E2As.

Evaluation of Thrombus Formation and Bacterial Adhesion on E2As NOrel Catheters in 9 Day Rabbit Model Intravascular NOrel catheters 50 were prepared using a dipcoating method. Two different solutions, namely topcoats 16 and 16' and active coat 14, were prepared to make the tri-layer catheters (see FIG. 5A). The topcoat 16, 16' solution was made up of E2As polymer dissolved in THF (150 mg/mL). The active coat 14 solution was made up of 25 wt % DBHD/N$_2$O$_2$, 10 wt % 5050DLG7E PLGA, and 65 wt % E2As polymer dissolved in THF with overall concentration of 150 mg/mL. Trilayer catheters 50 were prepared by dipcoating 5 base coats 16 of E2As solution, 25 coats of active solution 14, and 5 top coats 16' of E2As solution.

All catheters 50 were allowed to dry overnight under ambient conditions. Cured catheters 50 were removed from the mandrels and dried under vacuum for 48 hours. Catheters 50 had an i.d. of 1.20±0.07 mm and o.d. of 2.20±0.11 mm, as measured with a Mitutoyo digital micrometer.

The NOrel 50 and control catheters were implanted for 9 days in rabbits in cranial vena cava, as shown semi-schematically in FIG. 10 (1 catheter per rabbit). As mentioned above, FIG. 10 shows the NOrel or control catheter at reference numeral 100.

Following catheter implantation, rabbits were monitored closely for changes in behavior, weight, appearance, and activity level. All the rabbits recovered rapidly from surgical procedure, with only mild weight loss observed after 1-2 days post-surgery, but it returned to baseline in subsequent days with normal activity level. During the time of explantation, precautions were taken to remove the catheter from the vessel without disrupting the catheter surface. The vessel was cut longitudinally to carefully remove the whole catheter. The catheter was rinsed in sterile PBS buffer in 50 ml conical tubes. Any residual thrombus on the catheter was photographed. Explanted catheters were systematically cut into 1 cm sections starting at the distal tip for SEM imaging, bacterial adhesion testing, and post-surgery NO release measurements.

Figure 14:
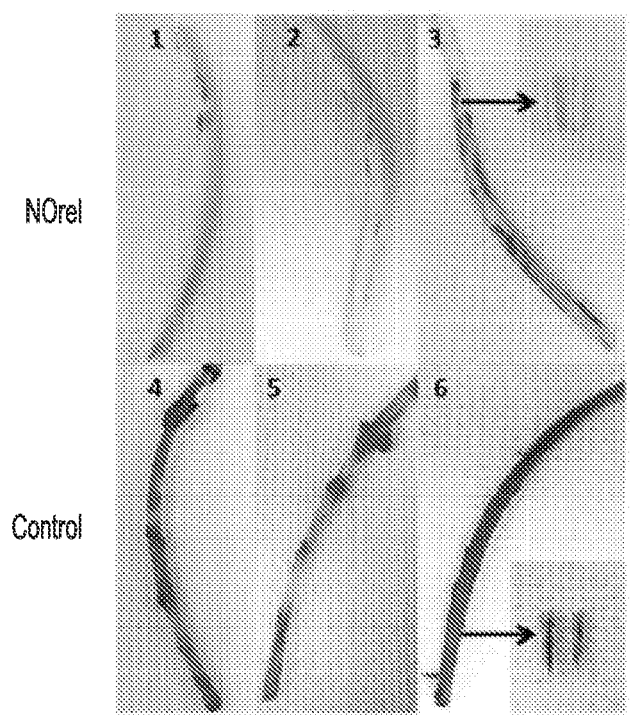
FIG. 14 shows photographs comparing control and NOrel catheters explanted after 9 days in rabbit (1-6 represent 6 different animals)
Figure 15:
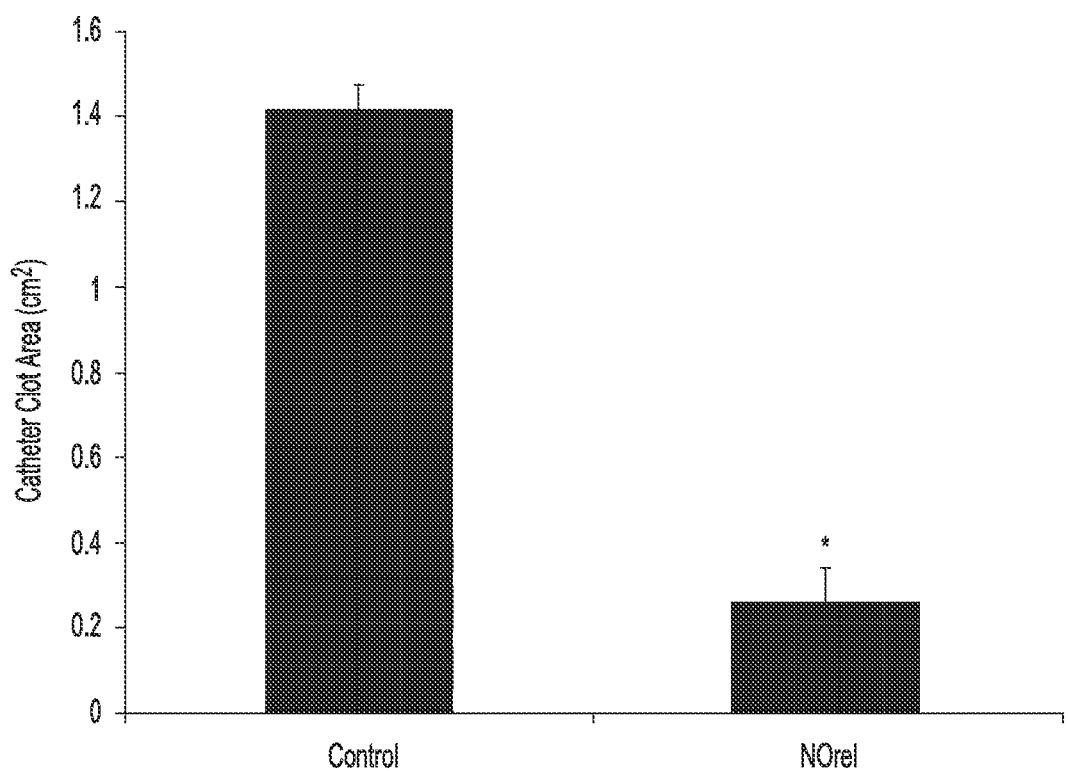
FIG. 15 shows quantitation of thrombus area as calculated with NIH ImageJ software using a 2D representation of thrombus (the data are means±SEM, *=p<0.05, control vs. NOrel catheters)
Figure 16:
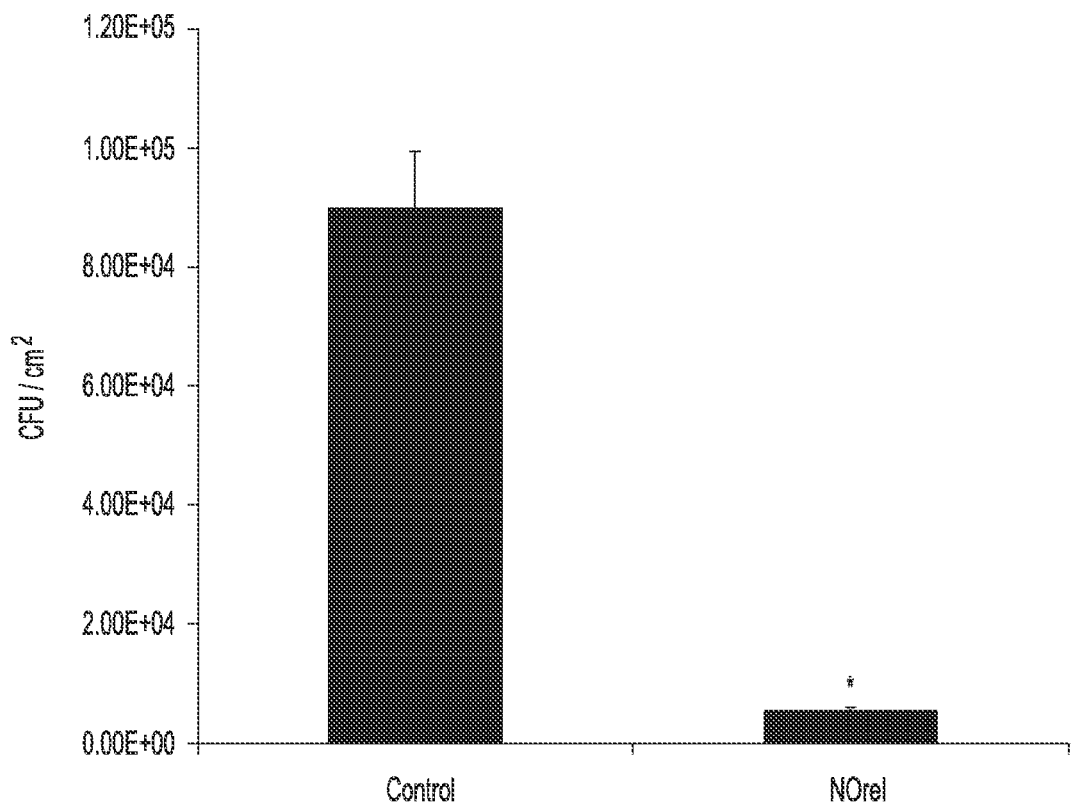
FIG. 16 is a comparison of bacterial adhesion (CFU/cm$^2$) on 1 cm piece of explanted catheters (the data are means±SEM, *=p<0.05, NOrel vs. control)

Surface thrombi on the explanted catheters were photographed, and the degree of thrombus area was quantitated using ImageJ imaging software from National Institutes of Health (Bethesda, Md.). FIG. 14 shows the images of the explanted control and NOrel catheters. The inset pictures show representative images of the clot formation on the interior walls of the catheter. These thrombi area measurements were quantitated and, as shown in FIG. 15, the thrombus area of the NOrel catheters was significantly reduced compared to the control catheters, 0.25±0.08 and 1.40±0.05 cm$^2$, respectively. One cm catheter section in 1 mL PBS was homogenized to detach the bacteria from the inner and outer catheter surfaces and cultured as described in experimental section above. The bacterial colonies were counted the following day and were represented as CFU/cm$^2$ in FIG. 16. A 1.3 log reduction (94% reduction) in bacterial adhesion was observed for NOrel catheters as compared to the controls.

Figure 17A:
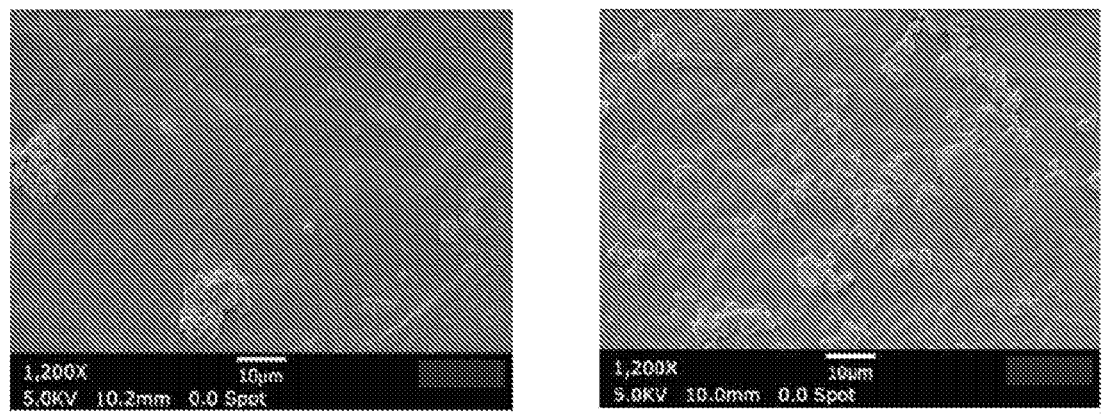
FIGS. 17A and 17B are representative scanning electron microscopy (SEM) images of explanted NOrel (FIG. 17A) and control (FIG. 17B) catheter surfaces after 9 day implantation in rabbit veins.
Figure 17B:
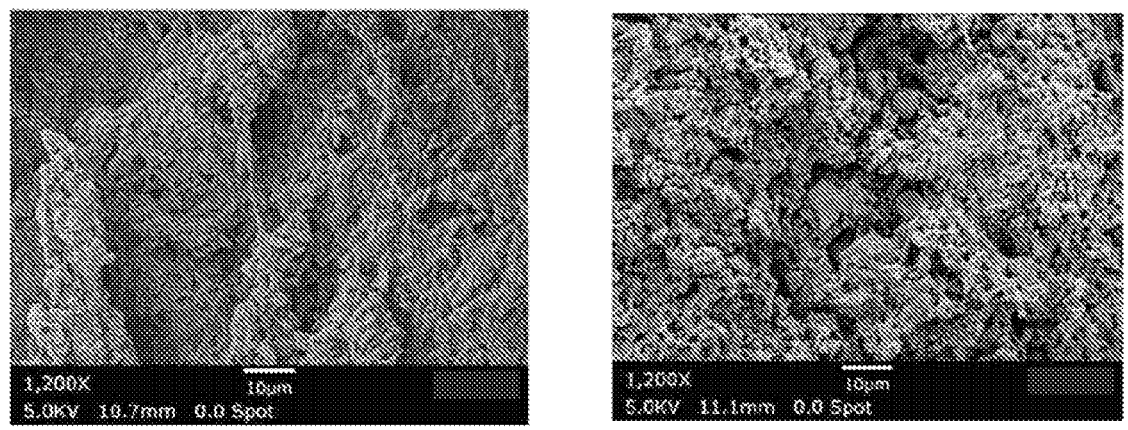

As show in the SEM images (FIGS. 17A and 17B), the NOrel catheters consistently showed significantly fewer adhered platelets than the control, with little gross thrombus formation (FIG. 14), but did show signs of adhered fibrin on the surface. Nitric oxide releasing surfaces have been reported to have high fibrinogen adsorption. In contrast, the E2As control catheters were covered with a thick layer of thrombus which made it difficult to distinguish between the various blood components (activated platelets, fibrin, and entrapped red blood cells, etc.) and adhered bacteria.

Figure 18:
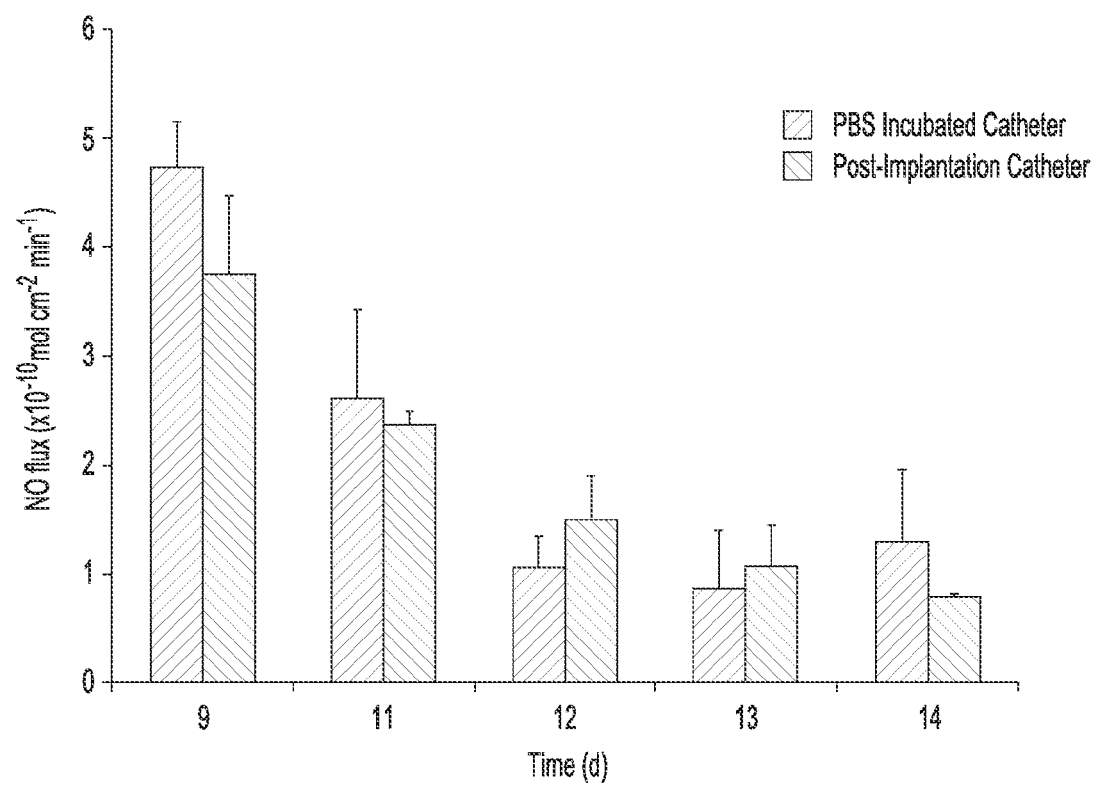
FIG. 18 shows a comparison of NO release profile of explanted catheter and catheter incubating at 37° C. in PBS.

Post-implanted catheters had a NO flux of 3.8±0.7×10$^{-10}$ mol cm$^{-2}$ min$^{-1}$ on the day of explantation, which is well within the normal range of NO from the endothelium. Post-implanted catheters continued to release NO for 5 days after explantation, and the flux levels were found to be similar to the catheters that had been continuously incubated in PBS at 37° C. as shown in FIG. 18. This data shows that NO release is not compromised due to blood exposure.

The present inventors have also developed formulations that can release NO for up to a 24 day period. FIG. 19 shows the complete NO release fluxes over a 24 day period for polymeric films prepared to contain 25 wt % DBHD/N$_2$O$_2$ with 5 wt %, 10 wt %, and 25 wt % of 6535DLG7E PLGA additives in SP-60D-20 polymer. SP-60D-20 is a polyurethane with a water uptake of ~20% (in between that of E2As and SP-60D-60). In FIG. 19, 5 wt % 6535DLG7E films are shown to release NO for 24 days; however, the fluxes were quite low (between 1 and 5×10$^{-10}$ mol cm$^{-2}$ min$^{-1}$). These low fluxes indicate that the 5 wt % PLGA is not adequate to compensate for the pH increase due to production of DBHD within the film. Increasing the PLGA to 25 wt % yields films that exhibit much higher fluxes over the 24 day period.

Conclusions

The present disclosure shows nitric oxide release from E2As NOrel coatings used on the inner walls of ECC circuits was able to attenuate the activation of the platelets while maintaining their functionality in a 4 hour ECC rabbit model and reduce clot area. The E2As-based NOrel catheters were implanted in rabbits for a 9 day period. The NOrel catheters were also found to significantly prevent clot formation and bacterial adhesion. These advantageous results demonstrate that NOrel materials may improve the hemocompatibility and antibacterial properties of a wide range of biomedical devices.

Still further, the present disclosure demonstrates, for the first time, that ester capped PLGA materials can advantageously be used as an additive within plasticized PVC films containing lipophilic dizeniumdiolate species, and the presence of the ester capped PLGA sustains the NO release for much longer time periods than possible without the additive. By using various pH probes, it was shown that the hydrolysis rates of specific ester capped PLGA species employed can control the NO release properties by influencing the pH within the organic films. Nitric oxide release from the present examples of ester capped PLGA-doped coatings used on the inner walls of ECC circuits was able to attenuate the activation of the platelets while maintaining their functionality. A significant reduction in the clot area was also seen as compared to the control ECC circuits. It is believed that examples of the present ester capped PLGA-doped NOrel PVC coatings may provide a breakthrough in long-term preservation of circulating platelets, an important goal for longer-term ECC situations, such as extracorporeal membrane oxygenation (ECMO).

It is to be understood that the ranges provided herein include the stated range and any value or sub-range within the stated range. For example, a range of about 5 wt % to about 30 wt % should be interpreted to include not only the explicitly recited limits of about 5 wt % to about 30 wt %, but also to include individual values, such as 7 wt %, 22.5 wt %, 29 wt %, etc., and sub-ranges, such as 8 wt %-25 wt %, 10 wt %-20 wt %, etc. Furthermore, when "about" or "approximately" or the like is/are utilized to describe a value, this is meant to encompass minor variations (up to +/−10%) from the stated value.

While several examples have been described in detail, it will be apparent to those skilled in the art that the disclosed examples may be modified. Therefore, the foregoing description is to be considered non-limiting.

What is claimed is:

1. A polymeric composition, comprising:
   a polymer matrix having at least one of a lipophilic discrete nitric oxide adduct or a polymeric nitric oxide adduct associated therewith, by: covalent attachment to the polymeric matrix; dispersion within the polymeric matrix; or both, with the at least one of the discrete nitric oxide adduct or the polymeric nitric oxide adduct capable of releasing nitrous oxide (NO); and an ester capped poly(lactide-co-glycolide) (PLGA) additive to at least one of increase, prolong, and control NO release rates from the at least one of the lipophilic discrete nitric oxide adduct or the polymeric nitric oxide adduct, the ester capped PLGA additive having a 65:35 ratio of lactic acid monomer to glycolic acid monomer.

2. The polymeric composition as defined in claim 1 wherein the polymer matrix comprises a hydrophobic polymer or a polymer with both hydrophobic and hydrophilic domains.

3. The polymeric composition as defined in claim 1 wherein the polymer matrix comprises at least one of poly(vinyl chloride), silicone rubbers, polyurethanes, polymethacrylates, polyacrylates, polycaprolactone, copolymers thereof, and mixtures thereof.

4. The polymeric composition as defined in claim 1 wherein the polymer matrix further comprises a plasticizer.

5. The polymeric composition as defined in claim 4 wherein the plasticizer comprises at least one of dioctyl sebacate, isopropyl palmitate, isopropyl isosterate, diisooctyl phthalate, o-nitrophenyloctyl ether, and mixtures thereof.

6. The polymeric composition as defined in claim 1 wherein the polymer matrix further comprises chromoionophores.

7. The polymeric composition as defined in claim 1 wherein the polymer matrix comprises poly(vinyl chloride).

8. The polymeric composition as defined in claim 1 wherein the polymer matrix comprises a polyurethane elastomer with poly(dimethylsiloxane) (PDMS) soft segments.

9. The polymeric composition as defined in claim 1 wherein:
the polymer matrix is poly(vinyl chloride) (PVC) or a polyurethane elastomer with poly(dimethylsiloxane) (PDMS) soft segments; and
the composition includes the lipophilic discrete nitric oxide (NO) adduct, the NO adduct being DBHD/$N_2O_2$ (diazeniumdiolated dibutylhexane diamine).

10. The polymeric composition as defined in claim 9 wherein:
the polymer matrix includes 65 wt % of: the PVC and dioctyl sebacate (DOS) in a 2:1 ratio; or the polyurethane elastomer with poly(dimethylsiloxane) (PDMS) soft segments;
the composition includes 25 wt % DBHD/$N_2O_2$; and the composition includes 10 wt % of the 6535DLG7E PLGA.

11. A polymeric device, comprising:
a base polymer layer;
a top polymer layer disposed on the base polymer layer; and
at least one active layer between the base polymer layer and the top polymer layer, and the at least one active intermediate layer including the polymeric composition as defined in claim 1.

12. A polymeric device, comprising:
a base polymer layer;
a top polymer layer disposed on the base polymer layer; and
at least one active layer between the base polymer layer and the top polymer layer, and the at least one active intermediate layer including the polymeric composition as defined in claim 9.

13. The polymeric device as defined in claim 12 wherein:
the base polymer layer is PVC or the polyurethane elastomer with poly(dimethylsiloxane) (PDMS) soft segments; and
the top polymer layer is: PVC and dioctyl sebacate (DOS) in a 1:2 ratio; or the polyurethane elastomer with poly(dimethylsiloxane) (PDMS) soft segments.

14. The polymeric device as defined in claim 13 wherein the polymeric device is extracorporeal circuit (ECC) tubing or an intravascular catheter.

15. A method for making an NO-releasing polymeric composition, comprising the steps of:
providing a polymer matrix;
dispersing at least one of a lipophilic discrete nitric oxide adduct and a polymeric nitric oxide adduct within the polymeric matrix, the at least one of the discrete nitric oxide adduct or the polymeric nitric oxide adduct capable of releasing nitrous oxide (NO); and
selecting an ester capped poly(lactide-co-glycolide) (PLGA) additive to at least one of increase, prolong, and control NO release rates from the at least one of the lipophilic discrete nitric oxide adduct or the polymeric nitric oxide adduct, the ester capped PLGA additive having a 65:35 ratio of lactic acid monomer to glycolic acid monomer and having a hydrolysis rate that substantially matches the rate of production of amine sites formed after loss of NO from the at least one of the discrete nitric oxide adduct or the polymeric nitric oxide adduct.

* * * * *